(12) United States Patent
Dana et al.

(10) Patent No.: US 9,670,277 B2
(45) Date of Patent: *Jun. 6, 2017

(54) COMPOSITIONS AND METHODS FOR TREATING INFLAMMATORY CONDITIONS OF THE OCULAR SURFACE

(75) Inventors: Reza Dana, Newton, MA (US); Daniel Saban, Raleigh, NC (US)

(73) Assignee: The Schepens Eye Reasearch Institute, Inc., Boston, MA (US)

( * ) Notice: Subject to any disclaimer, the term of this patent is extended or adjusted under 35 U.S.C. 154(b) by 12 days.

This patent is subject to a terminal disclaimer.

(21) Appl. No.: 14/001,594

(22) PCT Filed: Feb. 24, 2012

(86) PCT No.: PCT/US2012/026495
§ 371 (c)(1),
(2), (4) Date: Feb. 11, 2014

(87) PCT Pub. No.: WO2012/148547
PCT Pub. Date: Nov. 1, 2012

(65) Prior Publication Data
US 2014/0147449 A1    May 29, 2014

Related U.S. Application Data

(60) Provisional application No. 61/446,086, filed on Feb. 24, 2011.

(51) Int. Cl.
   *C07K 16/28*    (2006.01)
   *A61K 9/00*    (2006.01)
   *A61K 38/19*    (2006.01)
   *A61K 39/00*    (2006.01)

(52) U.S. Cl.
   CPC .......... *C07K 16/28* (2013.01); *A61K 9/0048* (2013.01); *A61K 38/195* (2013.01); *C07K 16/2866* (2013.01); *A61K 2039/505* (2013.01); *C07K 2317/76* (2013.01)

(58) Field of Classification Search
None
See application file for complete search history.

(56) References Cited

U.S. PATENT DOCUMENTS

2010/0285020 A1    11/2010   Aifantis et al.
2011/0104236 A1*    5/2011   Dana et al. ............... 424/429

FOREIGN PATENT DOCUMENTS

| JP | 2002284777 A | 3/2002 |
| WO | WO-2004033440 A1 | 4/2004 |
| WO | WO 2009025763 A2 * | 2/2009 |
| WO | WO-2009025763 A2 | 2/2009 |
| WO | WO-2009089036 A2 | 7/2009 |
| WO | WO-2009139853 A2 | 11/2009 |

OTHER PUBLICATIONS

Ma (Modern Drug Discovery 2004, 7(6).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Aagaard et al (Advanced Drug Delivery Reviews 59 (2007) 75-86).*
Warzocha et al (Leukemia and Lymphoma, Val. 24. pp. 267-281).*
Guido et al (Curr Med Chem. 2008;15(1):37-46).*
Vajdos et al. (J Mol Biol. Jul. 5, 2002;320(2):415-28 at 416).*
Brown et al. (J Immunol. May 1996;156(9):3285-91 at 3290 and Tables 1 and 2).*
Pilkington et al. "Inhibition of Generation of Cytotoxic T Lymphocyte Activity by a CCL19/Macrophage Inflammatory Protein (MIP)-3β Antagonist." *J. Biol. Chem.* 279.39(2004):40276-40282.

* cited by examiner

*Primary Examiner* — Brian J Gangle
*Assistant Examiner* — Andrea McCollum
(74) *Attorney, Agent, or Firm* — Mintz Levin Cohn Ferris Glovsky and Popeo, P.C.

(57) ABSTRACT

This application discloses ophthalmic formulations and methods for treating inflammatory disease and conditions of the ocular surface with one or more C—C chemokine receptor type 7 (CCR7) antagonists. The compositions may be formulated for subconjunctival or topical administration to the eye and are effective in the treatment of inflammatory disease and conditions of the ocular surface.

10 Claims, 8 Drawing Sheets

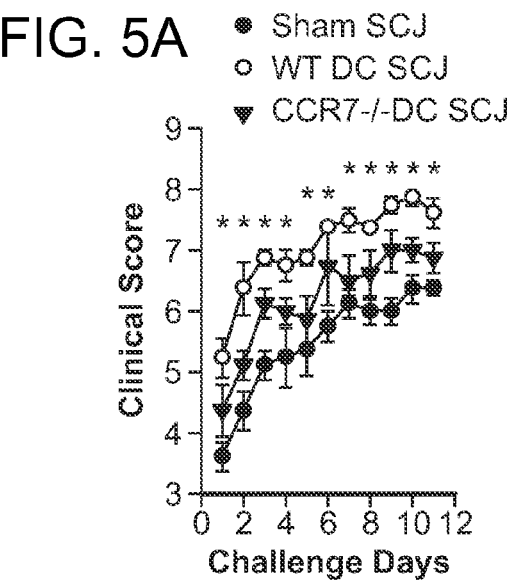
FIG. 5A
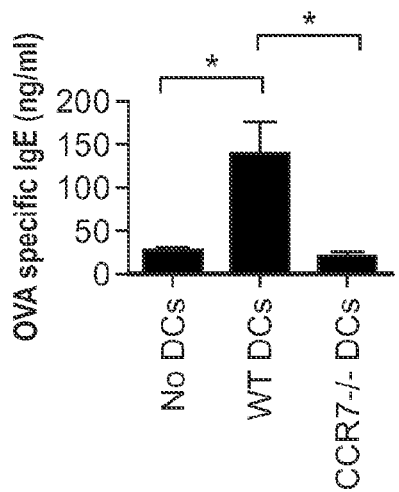
FIG. 5B
FIG. 5C
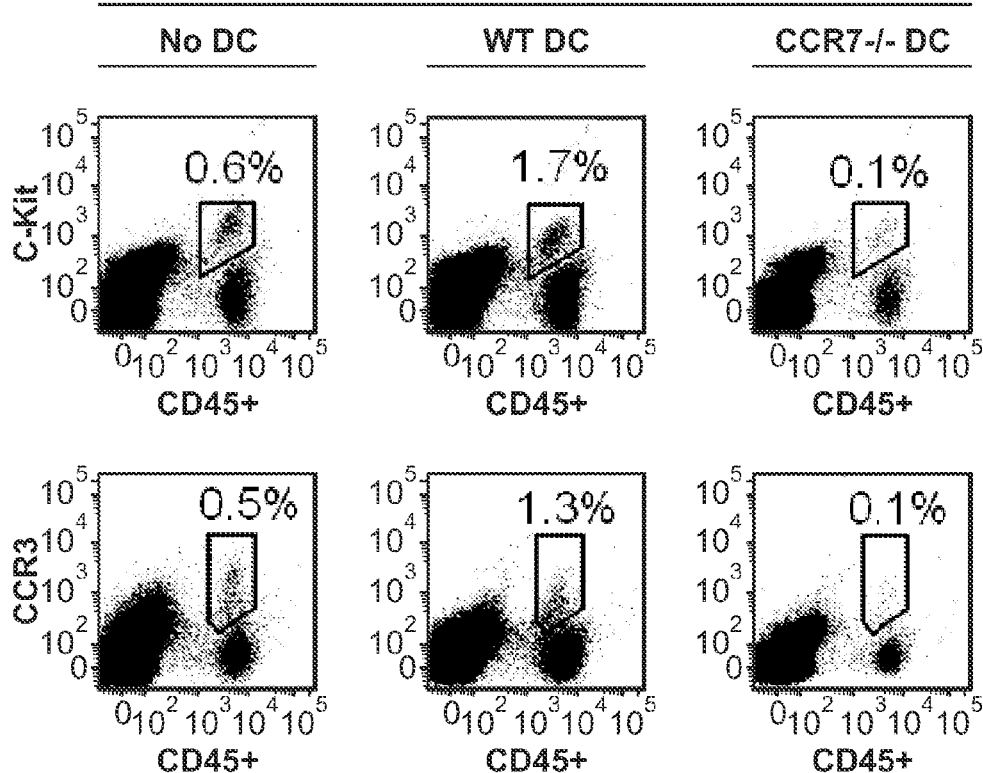

COMPOSITIONS AND METHODS FOR TREATING INFLAMMATORY CONDITIONS OF THE OCULAR SURFACE

RELATED APPLICATIONS

This application is a national stage application, filed under 35 U.S.C. §371, of International Application No. PCT/US2012/026495, filed Feb. 24, 2012, which claims the benefit of priority under 35 U.S.C. §119(e) to U.S. Provisional Application No. 61/446,086, filed Feb. 24, 2011, which are incorporated herein by reference in their entireties.

SEQUENCE LISTING

The instant application contains a Sequence Listing which has been filed electronically in ASCII format and is hereby incorporated by reference in its entirety. Said ASCII copy, created on Feb. 3, 2017, is named 36770-517N01US_ST25.txt and is 3,556 bytes in size.

FIELD OF THE DISCLOSURE

The present invention relates to compositions and methods for treating inflammatory conditions of the ocular surface.

BACKGROUND OF THE DISCLOSURE

Ocular surface inflammation is a leading cause of visual impairment worldwide, and is a result of conditions such as allergic conjunctivitis (AC). Some 30 million people in the U.S. alone suffer from AC. In addition, it is a primary reason for contact lens intolerance. Forms of AC include perennial and seasonal AC, and vision-threatening forms of vernal and atopic (kerato) conjunctivitis. Due to the widespread incidence of allergic conjunctivitis, there is a continuing need for the discovery of novel agents that are effective to ameliorate the symptoms of this condition.

SUMMARY OF THE DISCLOSURE

The present invention relates to pharmaceutical formulations for use in the treatment and prevention of inflammatory diseases and conditions of the ocular surface. The invention also provides for methods for the treatment and prevention of inflammatory diseases and conditions of the ocular surface (e.g., the cornea, conjunctiva, sclera, and/or eye lid) in a subject in need of such treatment by administering the formulations of the present invention directly to the eye or region of the eye of the subject. The subject is preferably a mammal in need of such treatment, e.g., a subject that has been diagnosed with an inflammatory disease of the ocular surface or a predisposition thereto. The mammal can be any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Methods are provided for treating an inflammatory condition of the ocular surface, the method comprising administering to the eye of a subject in need thereof an ophthalmic formulation comprising an effective amount of one or more C—C chemokine receptor type 7 (CCR7) antagonists. CCR7 antagonists may include proteins, nucleic acids, carbohydrates, antibodies, or any other molecules that decrease the effect of a CCR7, such as decrease the expression of or signaling effects of the receptor. The concentration of CCR7 antagonists may be from about 0.10% to 2.0% (w/v).

Suitable CCR7 antagonists include an anti-CCR7 antibody. The antagonist, e.g., CCR7-specific antibody, binds to the receptor (CCR7) on a cell expressing CCR7 in an ocular tissue. Alternatively, the CCR7 antagonist is an N-terminal truncation mutant of CCL19 and an N-terminal truncation mutant of CCL21.

Inflammatory conditions of the ocular surface include ocular inflammation, uveitis, scleritis, keratitis, retinitis, iritis, uveoretinitis, uveoscleritis, conjunctivitis, episcleritis, optic neuritis, retrobulbar neuritis, blepharitis, Mooren's ulcer and inflammatory ocular manifestations in allergies.

Optionally, the inflammatory condition of the ocular surface is an allergic condition of the ocular surface. Allergic conditions of the ocular surface include conjunctivitis, hay fever conjunctivitis, allergic conjunctivitis, perennial allergic conjunctivitis, seasonal allergic conjunctivitis, atopic conjunctivitis, vernal conjunctivitis, keratoconjunctivitis, atopic keratoconjunctivitis, vernal keratoconjunctivitis, allergic rhinoconjunctivitis, and giant papillary conjunctivitis, scleritis, blepharitis.

The pharmaceutical formulations of the present invention (e.g., one or more CCR7 antagonists) are formulated for ophthalmic delivery. For example, the pharmaceutical compositions are formulated for subconjunctival administration. Alternatively, the pharmaceutical compositions are formulated for topical administration to the eye or region of the eye. For example, the formulation may comprise one or more tear substitutes. The formulation alternatively comprises an ophthalmic lubricant.

The pH of the formulation is between 5.5 and 7. Preferably, the formulation is an aqueous formulation. The formulation is in the form of a single dose unit or in the form of a multi-dose system.

Methods for treating ocular surface inflammation are carried out by administering to the eye of a subject in need thereof an ophthalmic formulation comprising an effective amount of one or more C—C chemokine receptor type 7 (CCR7) antagonists.

Other methods for treating perennial allergic conjunctivitis are carried out by administering to the eye of a subject in need thereof an ophthalmic formulation comprising an effective amount of one or more C—C chemokine receptor type 7 (CCR7) antagonists.

Methods are provided for treating seasonal allergic conjunctivitis. The method comprises administering to the eye of a subject in need thereof an ophthalmic formulation comprising an effective amount of one or more C—C chemokine receptor type 7 (CCR7) antagonists.

The invention also provides methods for treating atopic keratoconjunctivitis comprising administering to the eye of a subject in need thereof an ophthalmic formulation comprising an effective amount of one or more C—C chemokine receptor type 7 (CCR7) antagonists.

Also provided are methods for treating atopic conjunctivitis. The methods comprise administering to the eye of a subject in need thereof an ophthalmic formulation comprising an effective amount of one or more C—C chemokine receptor type 7 (CCR7) antagonists.

A method for treating vernal keratoconjunctivitis is carried out by administering to the eye of a subject in need thereof an ophthalmic formulation comprising an effective amount of one or more C—C chemokine receptor type 7 (CCR7) antagonists.

Also provided are methods for treating vernal conjunctivitis. The methods comprise administering to the eye of a subject in need thereof an ophthalmic formulation comprising an effective amount of one or more C—C chemokine receptor type 7 (CCR7) antagonists.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth.

Throughout this application, the term "about" is used to indicate that a value includes the standard deviation of error for the device or method being employed to determine the value.

Reference to numeric ranges throughout this specification encompasses all numbers falling within the disclosed ranges. Thus, for example, the recitation of the range of about 1% to about 5% includes 1%, 2%, 3%, 4%, and 5%, as well as, for example, 2.3%, 3.9%, 4.5%, etc.

The use of the term "or" in the claims is used to mean "and/or" unless explicitly indicated to refer to alternatives only or the alternatives are mutually exclusive, although the disclosure supports a definition that refers to only alternatives and "and/or."

The term "aqueous" typically denotes an aqueous composition wherein the carrier is to an extent of >50%, more preferably >75% and in particular >90% by weight water.

A "patient," "subject," or "host" to be treated by the subject method refers to either a human or non-human animal, such the primates, mammals, and vertebrates described above.

The phrase "pharmaceutically acceptable" is art-recognized and refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Optionally, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "tear substitute" refers to molecules or compositions which lubricate, "wet," approximate the consistency of endogenous tears, aid in natural tear build-up, or otherwise provide temporary relief of dry eye symptoms and conditions upon ocular administration.

The invention provides a method of treating an inflammatory disease or condition of the eye. An "inflammatory disease or condition of the eye" is a disease or condition of the eye involving, exacerbated by, or caused by, inflammation.

The phrase "effective amount" is an art-recognized term, and refers to an amount of an agent that, when incorporated into a pharmaceutical composition of the present invention, produces some desired effect at a reasonable benefit/risk ratio applicable to any medical treatment. For example, the term refers to that amount necessary or sufficient to eliminate, reduce or maintain (e.g., prevent the spread of) a symptom of an inflammatory conditions of the ocular surface (e.g., FECD). One of skill in the art may empirically determine the effective amount of a particular agent without necessitating undue experimentation.

The term "preventing," when used in relation to a condition, such as ocular allergy is art-recognized, and refers to administration of a composition which reduces the frequency of, or delays the onset of, symptoms of a medical condition in a subject relative to a subject which does not receive the composition.

The term "treating" is an art-recognized term which refers to curing as well as ameliorating at least one symptom of any condition or disease.

Polynucleotides, polypeptides, antibodies, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide.

Although the phrase "nucleic acid molecule" primarily refers to the physical nucleic acid and the phrase "nucleic acid sequence" refers to the linear list of nucleotides of the nucleic acid molecule, the two phrases can be used interchangeably.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. GENBANK and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1 is a schematic, a series of cell sorting plots, and a bar chart illustrating that dendritic cells (DCs) mobilized from the ocular surface confer increased CCR7 expression in the lymphoid compartment of allergic conjunctivitis (AC)-induced mice.

FIG. 2 is a series of bar graphs showing that DCs from the ocular surface mount allergen-reactive Th2 responses in a CCR7-dependent manner Wild type (WT) DCs, CCR7−/− DCs, or no SCJ injection was administered into mice following adoptively transfer with OVA/Alum-primed T cells. After at least 10 days of once daily OVA topical challenges, host T cells were harvested from ipsi LN and recall stimulated in vitro with OVA. Control wells consisted of T cells from naïve mice stimulated with OVA in vitro as well. Supernatant was analyzed via enzyme-linked immunosorbent assay (ELISA) for IL-4, IL-13, and IL-5.

FIG. 4 is a series of line graphs, photomicrographs, and cell sorting plots demonstrating that DCs from the ocular surface lead to AC in a CCR7-dependent fashion.

FIG. 5 is a series of a line graph, a bar chart, and a cell plot showing that SCJ injection of WT, but not CCR7−/−, DCs augments allergic immune responses in CCR7−/− hosts. FIG. 5A is a line graph showing that SCJ injected WT DCs augment AC clinical signs in CCR7−/− hosts. WT DCs, CCR7−/− DCs, or sham HBSS were SCJ injected into mice following adoptive transfer with OVA/Alum-primed T cells (WT). All mice were challenged topically with OVA eye drops once daily and scored for at least 10 days. FIG. 5B is a bar chart showing SCJ injected WT DCs contribute to increased OVA-specific IgE to in CCR7−/− hosts. Blood was collected from hosts after at least 10 days of once daily OVA topical challenges. Sera was isolated and measured for OVA-specific IgE. FIG. 5C is a cell plot showing SCJ injected WT DCs lead to augmented conjunctival mast cells and eosinophils in CCR7−/− hosts. Conjunctivae were collected from AC-induced mice after at least 10 days of once daily OVA topical challenges and prepared for FACS analysis of mast cells (CD45+ c-Kit+) and eosinophils (CD45+ CCR3+). Data are derived from n=5 hosts per group, and figure represents multiple independent experiments. ($*p<0.05$)

FIG. 6 is a series of line graphs and photomicrographs showing that AC clinical signs are decreased by administration of topical CCR7 Ab blockade. Actively immunized mice were challenged once daily for 4 days with OVA eye drops containing 1% anti-CCR7 Ab or isotype control Ab.

FIG. 7 is a series of cell plots showing in vitro characterization of bone marrow derived DCs (BMDC).

FIG. 8 is a series of cell plots showing in vivo characterization of SCJ injected BMDCs in AC-induced mice.

DETAILED DESCRIPTION OF THE INVENTION

Non-infective, or allergic, conjunctivitis is characterized by ocular redness and itching and may involve mucus production in the eye. Allergic conjunctivitis is inflammation of the conjunctiva (the membrane covering the white part of the eye) due to allergy. Although allergens differ between patients, the most common cause is hay fever. Symptoms consist of redness (mainly due to vasodilation of the peripheral small blood vessels), oedema of the conjunctiva, itching and increased lacrimation (production of tears). If this is combined with rhinitis, the condition is termed allergic rhinoconjunctivitis. The symptoms are due to release of histamine and other active substances by mast cells, which stimulate dilation of blood vessels, irritate nerve endings and increase secretion of tears. Antigen activates the release of mediators of ocular allergy from the mast cells found in the eye. Histamine is one of these mediators, which is present in the secretory granules of mast cells and basophils and is formed by decarboxylation of histidine.

Conventionally, allergic conjunctivitis is treated using an ophthalmic preparation that contains a topical decongestant, either with or without an antihistamine agent. Treatment of allergic conjunctivitis may be by avoiding the allergen (e.g. avoiding grass in bloom during the "hay fever season") and treatment with antihistamines, either topical (in the form of eye drops), or systemic (in the form of tablets). Antihistamines, medication that stabilizes mast cells, and non-steroidal anti-inflammatory drugs (NSAIDs) are safe and usually effective. Unfortunately, current pharmacotherapies are only transiently effective and incapable of abolishing signs and symptoms. For example, drugs used to control the actions of histamine are not always effective. There, is thus a great need for agents that are effective in ameliorating the symptoms of this condition, but that do not generate the side-effects that detract from their attractiveness as therapeutic compounds.

Figure 10:
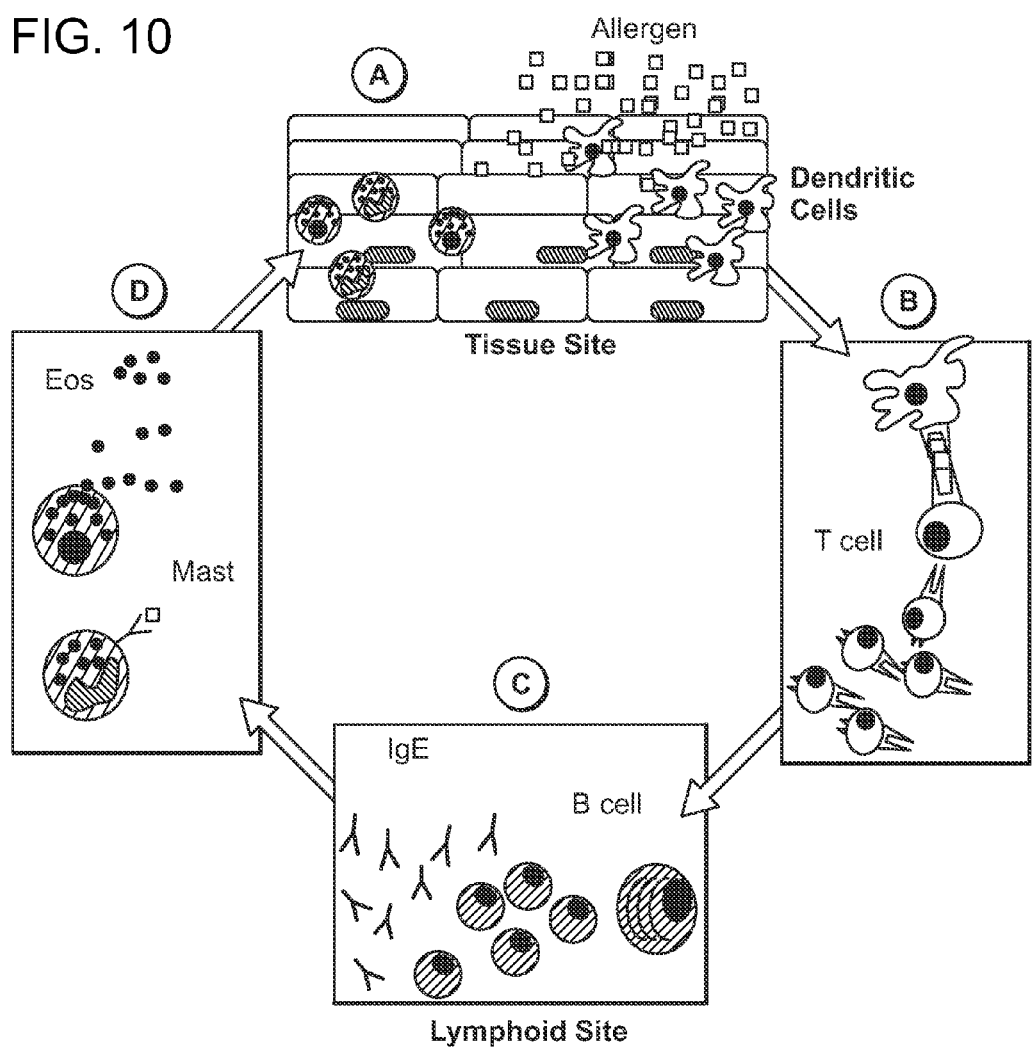
FIG. 10 is a schematic showing the immunopathogenesis of AC.

Antihistamines and mast cell stabilizers target IgE mediated released proinflammatory cytokines and histamines. However, this is preceded by important upstream activities not targeted by these drugs directly, namely the stimulation of T helper (h) 2 lymphocytes by dendritic cells (DC) (FIG. 10). Furthermore, DCs are required in both primary immune responses as well as secondary immune responses in allergy. Thus, primed mice subsequently deleted of their DCs are unable to mount allergic inflammation.

By capture and subsequent presentation of Ag to T helper (Th) lymphocytes, as well as being involved in driving T cell differentiation (e.g., Th1, Th2, and Th17), dendritic cells play a central role in the elicitation of adaptive immune responses. Unparalleled expression of MHC and costimulatory molecules (e.g., B7.1 and B7.2) allows mature DCs to be potent T cell stimulators. Likewise, DCs play a key role in activating T cells involved in allergic immunity (Novak N et al., 2010 J Allergy Clin Immunol, 125(1):50-9; Ohbayashi M et al., 2007 Exp Mol Pathol, 83(2):216-23; KleinJan A et al., 2006 J Allergy Clin Immunol, 118(5):1117-25; Soumelis V et al., 2002 Nat Immunol, 3(7):673-80; Lambrecht B N et al., 2000 J Clin Invest, 106(4):551-559; Lambrecht B N et al., 2000 J Immunol, 15; 164(6):2937-46; Sung S et al., 2001 J Immunol, 15; 166(2):1261-71; van Rijt L S et al., 2005 J Exp Med, 21; 201(6):981-91), e.g., in atopic dermatitis, allergic rhinitis, and perhaps best characterized in allergic asthma.

DCs are involved both at the level of Th2 sensitization to allergen, as well as in the progression of an allergic reaction and secondary immune responses via restimulation of effector/memory T cells. Indeed, degranulation and release of, for example, histamine and prostaglandins, makes activated mast cells and eosinophils important immune effectors in allergy. However, release of these proinflammatory factors by such leukocytes largely depends on direct and/or indirect help afforded by Th2 cells (Finkelman F D et al., 1988 J Immunol, 141(7):2335-41; Wills-Karp M et al., 1998 Science, 18; 282(5397):2258-61).

Although sensitization and differentiation of Th cells (e.g., Th2 in allergy) requires antigen presentation by DCs, engagement of these two cell types for this to occur, is not a simple matter. This is in part because mature DCs, which have captured Ag from inflamed tissue sites, must mobilize to the lymphoid compartment where large pools of T cells are found. One way in which this mobilization process is facilitated involves the CCR7-CCL19/21 chemokine axis (Sozzani S et al., 1998 J Immunol, 1; 161(3):1083-6; Dieu M C et al., 1998 J Exp Med, 20; 188(2):373-86). Mature DCs upregulate CCR7 at the inflamed tissue site and thereby respond chemotactically to a CCL21 gradient established by local lymphatic endothelial cells—a process which facilitates entry into lymphatics and consequently into the regional lymph node (LN; Gunn M D et al., 1999 J Exp Med, 189(3):451-60; Saeki H et al., 1999 J Immunol, 162(5): 2472-5). Furthermore, via CCL21 expression by high endothelial venules (HEV), which are positioned within the T cell-rich paracortex, CCR7 also helps traffic of DCs toward T cells within the LN (Sozzani S et al., 1998 J Immunol, 1; 161(3):1083-6; Dieu M C et al., 1998 J Exp Med, 20; 188(2):373-86; Gunn M D et al., 1999 J Exp Med, 189(3):451-60; Saeki H et al., 1999 J Immunol, 162(5): 2472-5).

However, prior to the invention described herein, it was unknown whether CCR7 expression on DCs at the ocular surface would promote allergic Th2 responses in allergic conjunctivitis (AC). Prior to the invention described herein, although reports have demonstrated DC infiltration in AC (Ohbayashi M et al., 2007 Exp Mol Pathol, 83(2):216-23), a role for DCs in AC had yet to be directly determined (Ishida W, et al., 2010 Mol Vis, 16:1280-5). In addition, other systems of chemotaxis including vascular endothelial growth factor receptor 3 (VEGFR3), have been implicated in mobilization from the ocular surface to LN in the initiation of adaptive immune responses (Hamrah P 2004 Exp Eye Res, 79(4):553-61; Chen L et al., 2004 Nat Med, 10(8):813-5; Hamrah P et al., 2003 Am J Pathol, 163(1):57-68). In contrast, CCR7 in ocular surface DCs has demonstrated to have a tolerogenic role, as shown in the corneal transplant model (Jin Y et al., 2010 Invest Ophthalmol Vis Sci. 51(2):816-21). Likewise, numerous other reports have shown in allergic asthma models that the CCR7-CCL19/21 axis is associated with the mediation of tolerance induction to allergen exposure (Sánchez-Sánchez N, et al., 2006 J Immunol, 176(9):5153-9; Yamashita N et al., 2006 J Allergy Clin Immunol, 117(5):1040-6; Grinnan D et al., 2006 J Allergy Clin Immunol, 118(6):1234-41; Hintzen G et al., 2006 J Immunol, 177(10):7346-54). For example, Hintzen reported a defect in DCs of CCR7−/− mice, but not in wild-type mice, in a model of airway-induced tolerance (Hintzen G et al., 2006 J Immunol, 177(10):7346-54). In addition, Grinnan, and Yamashita et al independently reported exaggerated allergen-induced airway inflammation in plt mutant mice (i.e., deficient in lymphoid CCL21 and CCL19; Yamashita N et al., 2006 J Allergy Clin Immunol, 117(5):1040-6; Grinnan D et al., 2006 J Allergy Clin Immunol, 118(6):1234-41; Hintzen G et al., 2006 J Immunol, 177(10):7346-54).

Described herein is the specific role in AC of CCR7 expression by DCs at the level of the ocular surface, and determine what effect blockade of CCR7 expression would have on the immunopathogenesis of this condition. As described in detail below, this important question was addressed in an established model of AC (Ozaki A et al., 2004 Microbiol Immunol, 48(1):39-48.). Described herein is an evaluation of allergy immunopathogenesis to exogenous DCs engrafted within the conjunctiva, along with the examination of the CCR7-CCL19/CCL21 system specifically on DCs in the ocular surface to allergen challenges. Data described herein demonstrate that while exogenous DCs augmented the progression of AC immunopathogenesis, these increased responses were completely abrogated in mice administered with CCR7 knockout DCs. Furthermore, this effect was mirrored when CCR7 antagonizing Ab was administered topically. The results provided herein demonstrate an important role for CCR7 expression by ocular surface DCs in promoting allergic immune responses. Thus, described herein is a strategy, involving CCR7 blockade, which is applied clinically for management of AC.

As described herein, elucidating chemokine mechanisms offers insight into the pathogenesis of ocular allergies, as they mediate dendritic cell (DC) mobilization from exposed sites to lymphocyte reservoirs located within lymphoid tissues to generate immunity. Thus, as described in detail below, the role of chemokine receptor CCR7 on DCs in AC was examined.

In short, as described in detail below, sorted T cells were harvested from wild-type (WT) C57BL/6 mice 14 d after an ovalbumin (OVA; 100 μg)/pertussis toxin (300 ng)/alum (1 mg) immunization. Naïve hosts were adoptively transferred with sorted T cells ($10^6$), and 1 d later also received a subconjunctival (sconj) injection with cultivated bone marrow (BM)-derived DCs ($10^5$), or sham PBS control. Hosts were then challenged with OVA eye drops (50 μg/ul) once daily for 12 days and post challenge slit-lamp evaluation was performed daily to follow development of clinical signs (e.g., chemosis, redness, tearing and lid edema). Additional parameters tested included mast cell infiltration, sera OVA specific IgE, and IL-4 and IL-13 levels to in vitro recall T cell stimulation.

As described in the examples below, BMDCs were qualified in vitro by their capacity to capture OVA, and proliferate T cells from immunized mice. In vivo qualification was demonstrated by instillation of FITC-conjugated OVA eye drops, which led to presence of subconj injected BMDCs that were FITC(+) in lymph nodes. Furthermore, OVA eye drops in adoptively transferred (WT T cells) mice with sconj injected BMDCs, versus sham injected PBS, showed significant augmentation of clinical signs ($p<0.05$). This was corroborated by a 2-fold increase in mast cell infiltration, 4-fold increase in IL-13 and IL-4 levels (p<0.05), and an 8-fold increase in sera IgE levels (p<0.05). Strikingly, this augmentation was completely reversed when OVA challenges were delivered to adoptively transferred hosts sconj injected with CCR7−/− BMDCs (rather than WT BMDCs), and this abrogation was consistent for all parameters tested. Moreover, this effect was similarly observed in adoptive transfer (of WT T cells) in CCR7−/− hosts, as sconj injection of CCR7−/− BMDCs (versus WT BMDCs) resulted in a significant reduction of AC clinical signs (p<0.05).

Thus, the model described herein highlights the critical role of CCR7 on DCs in AC immunopathogenesis, and suggests that blocking CCR7 may serve as a much needed and effective modality in AC therapy.

CCR7 Antagonist(s)

C—C chemokine receptor type 7 (CCR7) is a protein that in humans is encoded by the CCR7 gene. CCR7 has also recently been designated CD197 (cluster of differentiation 197).

The present invention discloses a method for treatment of inflammatory conditions of the ocular surface, including allergic conjunctivitis in humans, comprising ocular surface delivery (e.g., topical or subconjunctival administration) of a CCR7 antagonist(s), in combination with either a pharmaceutically suitable vehicle or another therapeutic agent. A CCR7 antagonist comprises any agent able to prevent CCR7 mediated signal transduction in cells, and may include, without limitation, CCL19 and CCL21 ligand, neutralizing anti-CCR7 antibody, soluble peptides able to bind CCR7, a blocking fusion protein or antibody against CCR7, and small molecule antagonist of CCR7.

Antagonists may include proteins, nucleic acids, carbohydrates, antibodies, or any other molecules that decrease the effect of a protein. As used herein, antagonists of CCR7 include any compound (agent) which modulates functions of CCR7, such as a protein, peptide, small organic molecule, nucleic acid, peptidomimetic, soluble chemokine receptor, and antibody.

For example, antagonists of CCR7 include an antibody which binds to CCR7 and inhibits the interaction between CCR7 and a chemokine (or ligand for CCR&), an agent (e.g., a fragment of CCR7) which binds to the chemokine receptor but does not elicit intracellular signaling events, and a compound which reduces or inhibits the CCR7 expression. Similarly, exemplary antagonists of a chemokine receptor includes an antibody which binds to the chemokine receptor and inhibits the interaction between the chemokine ligand and CCR7, an agent (e.g., a fragment of the chemokine receptor) which binds to CCR7 and prevents the interaction between CCR7 and the wild-type chemokine ligand, and a compound which reduces or inhibits the chemokine receptor expression.

Antibodies are exemplary antagonists. Antibodies may be polyclonal or monoclonal; intact or truncated, e.g., F(ab')2, Fab, Fv; xenogeneic, allogeneic, syngeneic, or modified forms thereof, e.g., humanized, chimeric, etc. Preferably, the antibody agonists is a neutralizing antibody (i.e., an antibody whose binding does not lead to the lysis or destruction of the CCR7 expressing cell).

Antibodies generation against CCR7 polypeptide can be obtained by administering the polypeptide or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, et al., Nature (1975) 256:495-497), the trioma technique, the human B-cell hybridoma technique (Kozbor, et al, Immunology Today (1983) 4:72), and the EBV-hybridoma technique (Cole, et al., Monoclonal Antibodies And Cancer Therapy, pp. 77-96, Alan R. Liss, Inc., 1985). Techniques for the production of single chain antibodies (U.S. Pat. No. 4,946,778) can also be adapted to produce single chain antibodies (e.g., against CCR7). Also, transgenic mice or other organisms including other mammals, may be used to express humanized antibodies.

Potential antagonists may include a small molecule (such as a peptidomimetic) that binds to CCR7, making it either more readily accessible or inaccessible to the other binding partner such that normal biological activity is enhanced or prevented. Examples of small molecules include, but are not limited to, small peptides or peptide-like molecules (e.g., a peptidomimetic). As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of CCR7.

In particular, potential antagonists also include soluble forms of a chemokine receptor (e.g., CCR7), such as fragments of the receptor which bind to CCR7 and prevent CCR7 from interacting with membrane bound (wild-type) chemokine receptor. Optionally, the fragments are derived from the intracellular or extracellular domains of CCR7. See, e.g., U.S. Publication No. 2011/0014128, incorporated by reference in its entirety.

Antagonists also encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl, sulfhydryl or carboxyl group. The CCR7 antagonist may be a thiadiazoledioxides and thiadiazoleoxides. See e.g., U.S. Pat. No. 7,691,856, incorporated herein by reference in its entirety by reference in its entirety. The CCR7 antagonist may be a tertiary amine containing a multiplicity of heteroaromatic substituents as described in U.S. Pat. No. 6,835,731 and U.S. Pat. No. 6,864,265, incorporated herein by reference in their entireties. The CCR7 antagonist may be a piperazinylpiperidine derivative as described in U.S. Pat. No. 7,678,798, incorporated herein by reference in its entirety.

Candidate antagonists can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant, and animal extracts are available or readily produced. Additionally, natural or synthetically produced libraries and compounds can be modified through conventional chemical, physical, and biochemical means. Known pharmacological agents may be subjected to directed or random chemical modifications, such as acylation, alkylation, esterification, and amidification, to produce structural analogs.

CCL19 and CCL21 Ligands

Chemokine (C—C motif) ligand 19 (CCL19) and Chemokine (C—C motif) ligand 21 (CCL21) are CCR7 ligands. CCL19 is a small cytokine belonging to the CC chemokine family that is also known as EBI1 ligand chemokine (ELC) and macrophage inflammatory protein-3-beta (MIP-3-beta). CCL19 is expressed abundantly in thymus and lymph nodes, with moderate levels in trachea and colon and low levels in stomach, small intestine, lung, kidney and spleen. This chemokine elicits its effects on its target cells by binding to the chemokine receptor chemokine receptor CCR7. CCL19 attracts certain cells of the immune system, including dendritic cells and antigen-engaged B cells, CCR7+ central-memory T-Cells. Human CCL19 is a 98 amino acid protein having the following sequence:

```
  1 malllalsll vlwtspaptl sgtndaedcc lsvtqkpipg yivrnfhyll
    ikdgcrvpav
 61 vfttlrgrql cappdqpwve riiqrlqrts akmkrrss (SEQ ID
    NO: 1)
```

Chemokine (C—C motif) ligand 21 (CCL21) is a small cytokine belonging to the CC chemokine family. This chemokine is also known as 6Ckine (because it has six conserved cysteine residues instead of the four cysteines typical to chemokines), exodus-2, and secondary lymphoid-tissue chemokine (SLC). The gene for CCL21 is located on human chromosome 9. CCL21 elicits its effects by binding to a cell surface chemokine receptor known as CCR7. Human CCL21 is an 134 amino acid protein having the following sequence:

```
                                                   (SEQ ID NO: 2)
  1 maqslalsll ilvlafgipr tqgsdggaqd cclkysqrki pakvvrsyrk qepslgcsip 61 ailflprkrs qaelcadpke lwvqqlmqhl dktpspqkpa qgcrkdrgas ktgkkgkgsk 121 gckrtersqt pkgp
```

N-terminal truncation mutants of CCL19 and CCL21 may be used as antagonists to CCR7. See, e.g., Pilkington et al, J Biol Chem. 2004 Sep. 24; 279(39):40276-82, incorporated herein by reference in its entirety. As described in Pilkington, N-terminal truncation mutants of CCL21 not only inhibit CCL21-mediated chemotaxis but also CCL19-mediated chemotaxis. Examples of N-terminal CCL19 mutants, which function as CCR7 antagonists, are described in Pilkington, and set forth below.

```
                                   (SEQ ID NO: 3)
CCL19         GANDAEDCC -COOH (SEQ ID NO: 4)
CCL19(2-83)   -ANDAEDCC -COOH (SEQ ID NO: 5)
CCL19(3-83)   --NDAEDCC -COOH (SEQ ID NO: 6)
CCL19(4-83)   ---DAEDCC -COOH
```

```
                                   (SEQ ID NO: 7)
CCD19(5-83)   ----AEDCC -COOH (SEQ ID NO: 8)
CCL19(6-83)   -----EDCC -COOH

CCL19(7-83)   ------DCC -COOH

CCL19(8-83)   -------CC -COOH
```

For example, the CCR7 antagonist(s) comprise an N-terminal truncation mutants of CCL19 and CCL21 wherein 1 to 25 of the N-terminal amino acids have been deleted. This includes, for example, N-terminal truncation mutants of CCL19 and CCL21 wherein the N-terminal amino acids 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 18, 1 to 19, 1 to 20, 1 to 21, 1 to 22, 1 to 23, 1 to 24, 1 to 25 have been deleted. The N-terminal truncation mutants of CCL19 and CCL21 may have sequence identity with the corresponding amino acids of SEQ ID NO: 1 and SEQ ID NO: 2 that is at least 80%, at least 85%, at least 90%, at least 95%, at least 97%, or at least 98%, such that the N-terminal truncation mutants retain CCR7 antagonism.

Inflammatory Conditions of the Ocular Surface

The invention provides a method of treating an inflammatory disease or condition of the ocular surface. An "inflammatory disease or condition of the ocular surface" is a disease or condition of the eye involving, exacerbated by, or caused by, inflammation.

The invention provides methods for the treatment of eye diseases and conditions, in particular eye diseases and conditions that affect the surface of the eye, such as inflammatory or allergic conditions. Such methods generally comprise a step of: topically administering to a subject's eye surface, an effective amount of a pharmaceutical composition of the invention. Inflammatory conditions of the eye may have any of a wide variety of causes, including trauma (e.g., surgery, laser procedure, accidental mechanical action), and chemical, infective, allergic or other causes. Alternatively, inflammation of the eye may be a manifestation of an eye disease or condition, or a manifestation of a systemic disease or condition.

Inflammatory diseases and conditions of the eye that can be treated according to the present invention include, but are not limited to, conjunctivitis, hay fever conjunctivitis, allergic conjunctivitis, perennial allergic conjunctivitis, seasonal allergic conjunctivitis, keratoconjunctivitis, vernal conjunctivitis, vernal keratoconjunctivitis, allergic rhinoconjunctivitis, atopic keratoconjunctivitis, and giant papillary conjunctivitis, ocular inflammation, uveitis, scleritis, keratitis, retinitis, iritis, uveoretinitis, uveoscleritis, conjunctivitis, episcleritis, optic neuritis, retrobulbar neuritis, blepharitis, Mooren's ulcer and inflammatory ocular manifestations in allergies. As described herein, compositions and methods are provided for treating allergic conditions of the ocular surface.

Methods of Use

The topical ophthalmic formulations of the present invention are useful to treat inflammatory conditions of the ocular surface. Thus, the invention also provides methods for the treatment of inflammatory conditions of the ocular surface in a subject in need of such treatment by administering the ophthalmic formulations of the present invention directly to the eye or region of the eye of the subject.

Pharmaceutical formulations comprising at least one CCR7 antagonist of the invention may be used for the treatment inflammatory conditions of the ocular surface. For example, the pharmaceutical compositions are formulated for topical administration to the eye (e.g., subconjunctival administration; eye drops). Optionally, the pharmaceutical compositions may further comprise a tear substitute.

Also provided are methods for treating inflammatory conditions of the ocular surface in a subject in need thereof comprising administering to the eye surface of the subject a pharmaceutical composition comprising an effective amount of at least one (e.g., 1, 2, 3, 4, 5, 6, 7, 8, etc.) CCR7 antagonist(s). Optionally, the administration of CCR7 antagonist(s) to the eye of a subject in need of treatment of inflammatory conditions of the ocular surface is also effective to mitigate or reduce one or more symptoms associated with a disease or condition of inflammatory conditions of the ocular surface. The subject is preferably a human, but may be another mammal, for example a dog, a cat, a rabbit, a mouse, a rat, or a non-human primate.

The formulations of the present invention contain an amount of CCR7 antagonist(s), and optionally one or more additional active ingredients, that is effective for the intended use. Particular dosages are also selected based on a number of factors including the age, sex, species and condition of the subject. Effective amounts can also be extrapolated from dose-response curves derived from in vitro test systems or from animal models. The term "effective amount" means an amount of CCR7 antagonist(s) that is sufficient to eliminate, reduce or maintain (e.g., prevent the spread of) a symptom as a result of a inflammatory condition of the ocular surface. The effective amount is the amount sufficient for the treatment or prevention of an inflammatory condition of the ocular surface. "Treatment" in this context refers to reducing or ameliorating at least one symptom as a result of an inflammatory condition of the ocular surface. "Prevention" in this context refers to a reduction in the frequency of, or a delay in the onset of, symptoms associated with a disease or condition, relative to a subject who does not receive the composition. The invention features methods of treating inflammatory conditions of the ocular surface in a subject comprising use of the formulations described above. For example, a method of treating inflammatory conditions of the ocular surface may comprise administering to the eye surface of the subject a pharmaceutical composition comprising an effective amount of at least one CCR7 antagonist and a tear substitute in a pharmaceutically acceptable carrier.

Ocular Surface Inflammation

The CCR7 antagonist(s) formulations of the invention are useful for the treatment ocular surface inflammation. For example, the pharmaceutical compositions are formulated for topical administration to the eye (e.g., subconjunctival administration; eye drops). The pharmaceutical compositions may further comprise a tear substitute.

The topical ophthalmic formulations of the present invention are useful for treatment of ocular surface inflammation. Thus, the invention also provides methods for the treatment of the inflammatory conditions in a subject in need of such treatment by administering the ophthalmic formulations of the present invention directly to the eye of the subject.

Methods are also provided for treating ocular surface inflammation in a subject in need thereof comprising administering to the eye surface of the subject a pharmaceutical composition comprising an effective amount of at least one (e.g., 1, 2, 3, 4, 5, 6, 7, 8, etc.) CCR7 antagonist.

Perennial Allergic Conjunctivitis

The CCR7 antagonist(s) formulations of the invention are useful for the treatment perennial allergic conjunctivitis. In one aspect, the pharmaceutical compositions are formulated for topical administration to the eye (e.g., subconjunctival administration; eye drops). For example, the pharmaceutical compositions may further comprise a tear substitute.

The topical ophthalmic formulations of the present invention are useful for treatment of perennial allergic conjunctivitis. Thus, the invention also provides methods for the treatment of the inflammatory conditions in a subject in need of such treatment by administering the ophthalmic formulations of the present invention directly to the eye of the subject.

Provided herein are methods for treating perennial allergic conjunctivitis in a subject in need thereof comprising administering to the eye surface of the subject a pharmaceutical composition comprising an effective amount of at least one (e.g., 1, 2, 3, 4, 5, 6, 7, 8, etc.) CCR7 antagonist.

Seasonal Allergic Conjunctivitis

The CCR7 antagonist(s) formulations of the invention are useful for the treatment seasonal allergic conjunctivitis. The pharmaceutical compositions are formulated for topical administration to the eye (e.g., subconjunctival administration; eye drops). For example, the pharmaceutical compositions may further comprise a tear substitute.

The topical ophthalmic formulations of the present invention are useful for treatment of seasonal allergic conjunctivitis. Thus, the invention also provides methods for the treatment of the inflammatory conditions in a subject in need of such treatment by administering the ophthalmic formulations of the present invention directly to the eye of the subject.

Methods are provided for treating seasonal allergic conjunctivitis in a subject in need thereof comprising administering to the eye surface of the subject a pharmaceutical composition comprising an effective amount of at least one (e.g., 1, 2, 3, 4, 5, 6, 7, 8, etc.) CCR7 antagonist.

Atopic Keratoconjunctivitis

The CCR7 antagonist(s) formulations of the invention are useful for the treatment atopic keratoconjunctivitis. The pharmaceutical compositions are formulated for topical administration to the eye (e.g., subconjunctival administration; eye drops). For example, the pharmaceutical compositions may further comprise a tear substitute.

The topical ophthalmic formulations of the present invention are useful for treatment of atopic keratoconjunctivitis. Thus, the invention also provides methods for the treatment of the inflammatory conditions in a subject in need of such treatment by administering the ophthalmic formulations of the present invention directly to the eye of the subject.

Methods are provided for treating atopic keratoconjunctivitis in a subject in need thereof comprising administering to the eye surface of the subject a pharmaceutical composition comprising an effective amount of at least one (e.g., 1, 2, 3, 4, 5, 6, 7, 8, etc.) CCR7 antagonist.

Atopic Conjunctivitis

The CCR7 antagonist(s) formulations of the invention are useful for the treatment atopic conjunctivitis. The pharmaceutical compositions are formulated for topical administration to the eye (e.g., subconjunctival administration; eye drops). For example, the pharmaceutical compositions may further comprise a tear substitute.

The topical ophthalmic formulations of the present invention are useful for treatment of atopic conjunctivitis. Thus, the invention also provides methods for the treatment of the inflammatory conditions in a subject in need of such treatment by administering the ophthalmic formulations of the present invention directly to the eye of the subject.

Methods are provided for treating atopic conjunctivitis in a subject in need thereof comprising administering to the eye surface of the subject a pharmaceutical composition comprising an effective amount of at least one (e.g., 1, 2, 3, 4, 5, 6, 7, 8, etc.) CCR7 antagonist.

Vernal Keratoconjunctivitis

The CCR7 antagonist(s) formulations of the invention are useful for the treatment vernal keratoconjunctivitis. The pharmaceutical compositions are formulated for topical administration to the eye (e.g., subconjunctival administration; eye drops). For example, the pharmaceutical compositions may further comprise a tear substitute.

The topical ophthalmic formulations of the present invention are useful for treatment of vernal keratoconjunctivitis. Thus, the invention also provides methods for the treatment of the inflammatory conditions in a subject in need of such treatment by administering the ophthalmic formulations of the present invention directly to the eye of the subject.

Methods are provided for treating vernal keratoconjunctivitis in a subject in need thereof comprising administering to the eye surface of the subject a pharmaceutical composition comprising an effective amount of at least one (e.g., 1, 2, 3, 4, 5, 6, 7, 8, etc.) CCR7 antagonist.

Vernal Conjunctivitis

The CCR7 antagonist(s) formulations of the invention are useful for the treatment vernal conjunctivitis. The pharmaceutical compositions are formulated for topical administration to the eye (e.g., subconjunctival administration; eye drops). For example, the pharmaceutical compositions may further comprise a tear substitute.

The topical ophthalmic formulations of the present invention are useful for treatment of vernal conjunctivitis. Thus, the invention also provides methods for the treatment of the inflammatory conditions in a subject in need of such treatment by administering the ophthalmic formulations of the present invention directly to the eye of the subject.

Methods are provided for treating vernal conjunctivitis in a subject in need thereof comprising administering to the eye surface of the subject a pharmaceutical composition comprising an effective amount of at least one (e.g., 1, 2, 3, 4, 5, 6, 7, 8, etc.) CCR7 antagonist.

Ophthalmic Formulations

Antagonists may be formulated in combination with a suitable pharmaceutical carrier. Such formulations comprise a therapeutically effective amount of the antagonist, and a pharmaceutically acceptable carrier (excipient). Such carriers include, but are not limited to, saline, buffered saline, dextrose, water, glycerol, ethanol, and combinations thereof. Formulation should suit the mode of administration, and is well within the skill of the art.

For example, the pharmaceutical compositions of the invention may comprise combinations of at least one (e.g., 1, 2, 3, 4, 5, 6, etc.) CCR7 antagonist(s). In one aspect, the pharmaceutical compositions are formulated for subconjunctival administration. For example, the pharmaceutical compositions are formulated for topical administration to the eye (e.g., subconjunctival administration; eye drops). The pharmaceutical compositions may further comprise a tear substitute.

The concentration of CCR7 antagonist(s) are from 0.10% to 10.0% (w/v), including but not limited to, from 0.1% to 10%, from 0.1% to 9.5%, from 0.1% to 9%, from 0.1% to 8.5%, from 0.1% to 8%, from 0.1% to 7.5%, from 0.1% to 7%, from 0.1% to 10%, from 0.1% to 6%, from 0.1% to 5.5%, from 0.1% to 5%, from 0.1% to 4.5%, from 0.1% to 4%, from 0.1% to 3.5%, from 0.1% to 3%, from 0.1% to 2.5%, from 0.1% to 2%, from 0.1% to 1.5%, from 0.1% to 1%, from 0.1% to 0.5%, from 0.2% to 10%, from 0.2% to 9.5%, from 0.2% to 9%, from 0.2% to 8.5%, from 0.2% to 8%, from 0.2% to 7.5%, from 0.2% to 7%, from 0.2% to 10%, from 0.2% to 6%, from 0.2% to 5.5%, from 0.2% to 5%, from 0.2% to 4.5%, from 0.2% to 4%, from 0.2% to 3.5%, from 0.2% to 3%, from 0.2% to 2.5%, from 0.2% to 2%, from 0.2% to 1.5%, from 0.2% to 1%, from 0.2% to 0.5%, from 0.5% to 10%, from 0.5% to 9.5%, from 0.5% to 9%, from 0.5% to 8.5%, from 0.5% to 8%, from 0.5% to 7.5%, from 0.5% to 7%, from 0.5% to 10%, from 0.5% to 6%, from 0.5% to 5.5%, from 0.5% to 5%, from 0.5% to 4.5%, from 0.5% to 4%, from 0.5% to 3.5%, from 0.5% to 3%, from 0.5% to 2.5%, from 0.5% to 2%, from 0.5% to 1.5%, from 0.5% to 1%, from 1% to 10%, from 1% to 9.5%, from 1% to 9%, from 1% to 8.5%, from 1% to 8%, from 1% to 7.5%, from 1% to 7%, from 1% to 10%, from 1% to 6%, from 1% to 5.5%, from 1% to 5%, from 1% to 4.5%, from 1% to 4%, from 1% to 3.5%, from 1% to 3%, from 1% to 2.5%, from 1% to 2%, from 1% to 1.5%, from 2% to 10%, from 2% to 9.5%, from 2% to 9%, from 2% to 8.5%, from 2% to 8%, from 2% to 7.5%, from 2% to 7%, from 2% to 10%, from 2% to 6%, from 2% to 5.5%, from 2% to 5%, from 2% to 4.5%, from 2% to 4%, from 2% to 3.5%, from 2% to 3%, from 2% to 2.5%, from 3% to 10%, from 3% to 9.5%, from 3% to 9%, from 3% to 8.5%, from 3% to 8%, from 3% to 7.5%, from 3% to 7%, from 3% to 10%, from 3% to 6%, from 3% to 5.5%, from 3% to 5%, from 3% to 4.5%, from 3% to 4%, from 3% to 3.5%, from 4% to 10%, from 4% to 9.5%, from 4% to 9%, from 4% to 8.5%, from 4% to 8%, from 4% to 7.5%, from 4% to 7%, from 4% to 10%, from 4% to 6%, from 4% to 5.5%, from 4% to 5%, from 4% to 4.5%, from 5% to 10%, from 5% to 9.5%, from 5% to 9%, from 5% to 8.5%, from 5% to 8%, from 5% to 7.5%, from 5% to 7%, from 5% to 10%, from 5% to 6%, and from 5% to 5.5%.

Preferably, the pharmaceutical compositions according to the present invention will be formulated as solutions, suspensions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions.

Any of a variety of carriers may be used in the formulations of the present invention including water, mixtures of water and water-miscible solvents, such as C1- to C7-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. The concentration of the carrier is, typically, from 1 to 100000 times the concentration of the active ingredient. Additional ingredients that may be included in the formulation include tonicity enhancers, preservatives, solubilizers, non-toxic excipients, demulcents, sequestering agents, pH adjusting agents, co-solvents and viscosity building agents.

For the adjustment of the pH, preferably to a physiological pH, buffers may especially be useful. The pH of the present solutions should be maintained within the range of 4.0 to 8.0, more preferably about 4.0 to 6.0, more preferably about 6.5 to 7.8. Suitable buffers may be added, such as boric acid, sodium borate, potassium citrate, citric acid, sodium bicarbonate, TRIS, and various mixed phosphate buffers (including combinations of Na2HPO4, NaH2PO4 and KH2PO4) and mixtures thereof. Borate buffers are preferred. Generally, buffers will be used in amounts ranging from about 0.05 to 10 percent by weight.

Tonicity is adjusted if needed typically by tonicity enhancing agents. Such agents may, for example be of ionic and/or non-ionic type. Examples of ionic tonicity enhancers are alkali metal or earth metal halides, such as, for example, CaCl2, KBr, KCl, LiCl, NaI, NaBr or NaCl, Na2SO4 or boric acid. Non-ionic tonicity enhancing agents are, for example, urea, glycerol, sorbitol, mannitol, propylene glycol, or dextrose. The aqueous solutions of the present invention are typically adjusted with tonicity agents to approximate the osmotic pressure of normal lachrymal fluids which is equivalent to a 0.9%±0.1% solution of sodium chloride or a 2.5%±0.3% solution of glycerol. An osmolality of about 225 to 400 mOsm/kg is preferred, more preferably 280 to 320 mOsm.

The topical formulations additionally comprise a preservative. A preservative may typically be selected from a quaternary ammonium compound such as benzalkonium chloride, benzoxonium chloride or the like. Benzalkonium chloride is better described as: N-benzyl-N—($C_8$-$C_{18}$ alkyl)-N,N-dimethylammonium chloride. Examples of preservatives different from quaternary ammonium salts are alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sodium perborate, GERMAL®II or sorbic acid. Preferred preservatives are quaternary ammonium compounds, in particular benzalkonium chloride or its derivative such as POLYQUAD (see U.S. Pat. No. 4,407,791), alkyl-mercury salts and parabens. Where appropriate, a sufficient amount of preservative is added to the ophthalmic composition to ensure protection against secondary contaminations during use caused by bacteria and fungi.

Alternatively, the topical formulations of this invention do not include a preservative. Such formulations would be useful for patients who wear contact lenses, or those who use several topical ophthalmic drops and/or those with an already compromised ocular surface (e.g. dry eye) wherein limiting exposure to a preservative may be more desirable.

The topical formulation may additionally require the presence of a solubilizer, in particular if the active or the inactive ingredients tends to form a suspension or an emulsion. A solubilizer suitable for an above concerned composition is for example selected from the group consisting of tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin), polysorbate 20, polysorbate 80 or mixtures of those compounds. A specific example of an especially preferred solubilizer is a reaction product of castor oil and ethylene oxide, for example the commercial products CREMAPHOR EL® or CREMAPHOR RH40®. Reaction products of castor oil and ethylene oxide have proved to be particularly good solubilizers that are tolerated extremely well by the eye. Another preferred solubilizer is selected from tyloxapol and from a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient. The formulations may comprise further non-toxic excipients, such as, for example, emulsifiers, wetting agents or fillers, such as, for example, the polyethylene glycols designated 200, 300, 400 and 600, or CARBOWAX® designated 1000, 1500, 4000, 6000 and 10000. The amount and type of excipient added is in accordance with the particular requirements and is generally in the range of from approximately 0.0001 to approximately 90% by weight.

Other compounds may also be added to the formulations of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

The at least one CCR7 antagonist(s) may be administered by the use of or in the form of hydrogels, drug-eluting contact lenses, and nanosystems (liposomal systems, dendrimers, solid biodegradable nanoparticles, nanogels), and/or irrigating solutions.

Ophthalmic formulations, eye ointments, creams, salves, powders, solutions and the like, are also contemplated as being within the scope of this invention.

Furthermore, various other delivery systems are known and can be used to administer the at least one CCR7 antagonist(s) or a pharmaceutical compositions comprising the at least one CCR7 antagonist(s). The pharmaceutical composition of the present invention can be administered by any suitable route including, orally, subcutaneously, parenterally, intravenously, local injection, subconjunctivally, intranasal, intradermal, and sublingual.

Eye Drops

The use of CCR7 antagonist(s) in the eyedrop mode for treatment of inflammatory conditions of the ocular will enhance their effect by alleviating the bioavailability issue seen in systemic administration.

The eye drop may be formulated with or without one or more tear substitutes. Also provided are pharmaceutical compositions comprising an effective amount of one or more (e.g., 1, 2, 3, 4, 5, 6, 7, 8, 9, etc.) CCR7 antagonist(s) and a tear substitute in a pharmaceutically acceptable carrier for the treatment of inflammatory conditions of the ocular surface. The CCR7 antagonist(s) and tear substitute may act synergistically to provide a longer dwell time of the CCR7 antagonist(s) on the ocular surface, thus increasing duration and efficacy of action.

A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as carbomer 934P, carbomer 941, carbomer 940 and carbomer 974P. Many such tear substitutes are commercially available, which include, but are not limited to cellulose esters such as BION TEARS®, CELLUVISC®, GENTEAL®, OCCUCOAT®, REFRESH®, TEARGEN II®, TEARS NATURALE®, TEARS NATURAL II®, TEARS NATURALE FREE®, and THERATEARS®; and polyvinyl alcohols such as AKWA TEARS®, HYPOTEARS®, MOISTUREEYES®, MURINE LUBRICATING®, and VISINE TEARS®. Tear substitutes may also be comprised of paraffins, such as the commercially available LACRI-LUBE® ointments. Other commercially available ointments that are used as tear substitutes include LUBRIFRESH PM®, MOISTUREEYES PM® and REFRESH PM®.

In one aspect, the tear substitute contains hydroxypropylmethylcellulose. The tear substitute is GENTEAL® lubricating eye drops. GENTEAL® (CibaVision—Novartis) is a sterile lubricant eye drop containing hydroxypropyl methylcellulose 3 mg/g and preserved with sodium perborate.

The pharmaceutical compositions of the invention may comprise combinations of one or more CCR7 antagonist(s) and one or more tear substitutes.

The pharmaceutical compositions of the invention may comprise combinations of at least two CCR7 antagonist(s) and a tear substitute. The pharmaceutical compositions of the invention may comprise combinations of at least three CCR7 antagonist(s) and a tear substitute. Alternatively, the pharmaceutical compositions of the invention may comprise combinations of at least four CCR7 antagonist(s) and a tear substitute.

The topical formulations of the invention may comprise a CCR7 antagonist(s) and a combination of at least two tear substitutes. The topical formulations of the invention may comprise a CCR7 antagonist(s) and a combination of at least three tear substitutes. Alternatively, the topical formulations of the invention may comprise a CCR7 antagonist(s) and a combination of at least four tear substitutes.

Therapeutic Administration

The effective amount of the active agents in the formulation will depend on absorption, inactivation, and excretion rates of the drug as well as the delivery rate of the compound from the formulation. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of any compound of the present invention will vary depending on the symptoms, age and other physical characteristics of the patient, the nature and severity of the disorder to be treated or prevented, the degree of comfort desired, the route of administration, and the form of the supplement. Any of the subject formulations may be administered in a single dose or in divided doses. Dosages for the formulations of the present invention may be readily determined by techniques known to those of skill in the art or as taught herein.

An effective dose or amount, and any possible effects on the timing of administration of the formulation, may need to be identified for any particular formulation of the present invention. This may be accomplished by routine experiment as described herein. The effectiveness of any formulation and method of treatment or prevention may be assessed by administering the formulation and assessing the effect of the administration by measuring one or more indices associated with the efficacy of the active agent and with the degree of comfort to the patient, as described herein, and comparing the post-treatment values of these indices to the values of the same indices prior to treatment or by comparing the post-treatment values of these indices to the values of the same indices using a different formulation.

The precise time of administration and amount of any particular formulation that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

The combined use of several active agents formulated into the compositions of the present invention may reduce the required dosage for any individual component because the onset and duration of effect of the different components may be complimentary. In such combined therapy, the different active agents may be delivered together or separately, and simultaneously or at different times within the day.

Packaging

The formulations of the present invention may be packaged as either a single dose product or a multi-dose product. The single dose product is sterile prior to opening of the package and all of the composition in the package is intended to be consumed in a single application to one or both eyes of a patient. The use of an antimicrobial preservative to maintain the sterility of the composition after the package is opened is generally unnecessary.

Multi-dose products are also sterile prior to opening of the package. However, because the container for the composition may be opened many times before all of the composition in the container is consumed, the multi-dose products must have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP") and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing.")

The use of a single dose packaging arrangement eliminates the need for an antimicrobial preservative in the compositions, which is a significant advantage from a medical perspective, because conventional antimicrobial agents utilized to preserve ophthalmic compositions (e.g., benzalkonium chloride) may cause ocular irritation, particularly in patients suffering from dry eye conditions or pre-existing ocular irritation. However, the single dose packaging arrangements currently available, such as small volume plastic vials prepared by means of a process known as "form, fill and seal", have several disadvantages for manufacturers and consumers. The principal disadvantages of the single dose packaging systems are the much larger quantities of packaging materials required, which is both wasteful and costly, and the inconvenience for the consumer. Also, there is a risk that consumers will not discard the single dose containers following application of one or two drops to the eyes, as they are instructed to do, but instead will save the opened container and any composition remaining therein for later use. This improper use of single dose products creates a risk of microbial contamination of the single dose product and an associated risk of ocular infection if a contaminated composition is applied to the eyes.

While the formulations of this invention are preferably formulated as "ready for use" aqueous solutions, alternative formulations are contemplated within the scope of this invention. Thus, for example, the active ingredients, surfactants, salts, chelating agents, or other components of the ophthalmic solution, or mixtures thereof, can be lyophilized or otherwise provided as a dried powder or tablet ready for dissolution (e.g., in deionized, or distilled) water. Because of the self-preserving nature of the solution, sterile water is not required.

Kits

This invention provides kits for the packaging and/or storage and/or use of the formulations described herein, as well as kits for the practice of the methods described herein. Thus, for example, kits may comprise one or more containers containing one or more ophthalmic solutions, tablets, or capsules of this invention. The kits can be designed to facilitate one or more aspects of shipping, use, and storage.

The kits may optionally include instructional materials containing directions (i.e., protocols) disclosing means of use of the formulations provided therein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g. CD ROM), and the like. Such media may include addresses to internet sites that provide such instructional materials.

Example 1: Blocking CCR7 at the Ocular Surface Impairs the Pathogenic Contribution of Dendritic Cells in Allergic Conjunctivitis CCR7 plays a key role in mobilizing tissue DCs to the lymphoid compartment for consequent elicitation of adaptive immunity. However, prior to the invention described herein, the CCR7-CCL19/CCL21 system in the ocular surface was poorly understood, as is the precise role of DCs in AC immunopathogenesis. As described in detail below, interfering with CCR7 function inhibits the progression of atopic conditions, e.g., allergic conjunctivitis (AC).

Briefly, T cells from ovalbumin (OVA)-primed mice were adoptively transferred into wild-type (WT) hosts. Exogenous WT (eGFP+) versus CCR7−/− DCs were engrafted subconjunctivally (SCJ) and hosts were challenged with OVA (Texas-Red+) eye-drops. AC immunopathogenesis was evaluated via clinical examinations, infiltration of mast cells and eosinophils, Th2 reactivity, and serum IgE. AC was also assessed in actively immunized mice challenged with OVA eye drops containing 1% anti-CCR7 Ab or isotype control. As described in detail below, in eye draining lymph nodes (LN), OVA+ SCJ engrafted WT DCs conferred upregulated CCR7 and caused augmentation of clinical signs. This was corroborated by increased conjunctival infiltration, Th2 cytokines in LN, and serum OVA-specific IgE. Strikingly, this was completely reversed with SCJ engrafted CCR7−/− DCs in all parameters tested. Furthermore, topical Ab blockade of CCR7 in actively immunized mice significantly inhibited AC. Thus, ocular surface DCs via their CCR7 expression contribute to the immunopathogenesis of AC, thereby allowing significant inhibition of this experimental condition via topical CCR7 Ab blockade.

Mice and Anesthesia

C57BL/6 male mice 8-12 wk old were purchased from Charles River Laboratories (Wilmington, Mass.). CCR7 knockout mice (on a C57BL/6 background) were provided by Andrew Luster (Massachusetts General Hospital, Boston, Mass.) and Martin Lipp (Maz-Delbrueck-Center of Molecular Medicine, Berlin, Germany) Mice were housed in a specific pathogen-free environment at the Schepens Eye Research Institute animal facility. All procedures were approved by the Institutional Animal Care and Use Committee, and all animals were treated according to the ARVO Statement for the Use of Animals in Ophthalmic and Vision Research. Anesthesia was used for all surgical procedures with i.p. administered ketamine/xylazine suspensions (120 and 20 mg/kg, respectively).

Generation of Bone Marrow Derived DC (BMDC)

BMDCs were generated as previously described (Kuipers H et al., 2009 J Leukoc Biol. January; 85(1):64-70). Briefly, femurs and tibiae were collected from freshly euthanized mice. BM cells were seeded at $2\times10^5$/ml in RPMI 1640 (BioWitthaker, Walkersville, Md.) supplemented with 10% FBS, 1% penicillin/streptomycin, plus 20 ng/ml mouse GM-CSF (Biolegend, San Diego, USA) at 37° C. with 5% carbon dioxide. Medium was changed on day 4, and non- and loosely-adherent cells were collected on day 7 and thoroughly washed.

T Cell Adoptive Transfer

T cells for adoptive transfer were obtained from donor wild-type (WT) C57BL/6 mice that were immunized once i.p. with a 100 ul suspension containing 1 mg aluminum hydroxide (Sigma Aldrich, St. Louis, USA) diluted in HBSS, 300 ng pertussis toxin (Sigma Aldrich), and 100 ug ovalbumin (Sigma Aldrich). Donor mice 2 wk post immunization, a time-point consistent with high OVA-specific IgE titers in the sera, were euthanized and spleens were collected. Donor spleens were prepared into single cell suspensions by tissue press using a sterile 70 um sieve, and cells were then treated with red blood cell lysis buffer according to manufacturer's instructions (Sigma Aldrich) and washed thoroughly. Donor T cells were enriched for via MACS sorting using anti-CD90.2 Ab according to manufacturer's instructions (Miltenyi Biotec, Auburn, USA). The sorted donor population was then enumerated via trypan blue exclusion assay, and donor T cells were set at a concentration $1\times10^7$/ml of sterile HBSS. Recipient mice were adoptively transferred IV with $1\times10^6$ donor T cells.

Induction of Allergic Conjunctivitis (AC)

OVA primed T cells were prepared as described above, and $1\times10^6$ T cells were adoptively transferred into naïve hosts. Host mice were then anesthetized 16 hr later for unilateral injection of cells into the subconjunctival space as previously described (Fukuda K et al., 2009 J Allergy Clin Immunol. October; 124(4):827-33). Injection volume was 10 ul of sterile HBSS and contained $1\times10^5$ BMDCs. Challenge via topical OVA instillation (250 ug/5 ul eye drop) was administered immediately following subconjunctival (SCJ) injection, and then challenged additionally (to account for significant tearing post SCJ injection) twice more in 20 minute intervals. Challenges were subsequently administered once daily, for at least 10 days. In some experiments (FITC or TEXAS RED®)-conjugated OVA (Sigma Aldrich) was used for topical challenges.

AC Clinical Scoring

The AC clinical scoring procedure has been described previously (Reyes N J, et al., 2010 Int Immunol. August; 22(8):627-36), and performed here in a masked fashion by two independent observers. Briefly, scoring was performed 20 min post challenge and done once daily from day 1 (i.e. 24 hr following SCJ injection) to at least day 10. Mice were examined biomicroscopically based on four independent parameters, which include: 1) lid swelling; 2) tearing; 3) chemosis; and 4) conjunctival vasodilation (redness). Each parameter was ascribed 0 (i.e. absent) to 3+ points (i.e. maximal) and were summed to yield a maximum score of 12+.

OVA Specific IgE Quantitation

Blood was collected and kept at room temperature to allow coagulation. Sera was separated via centrifugation, and then collected and pooled. Aliquoted samples were immediately stored at −30° C. Aliquots were thawed at room temperature and diluted serially from 1:5 to 1:25. Samples were analyzed in duplicate or triplicate using a 96-well format using an OVA specific mouse IgE ELISA kit, (AbD Serotec, Raleigh, USA) carried out according to manufacturer's instructions.

Conjunctival Mast Cell and Eosinophil Quantitation

After 20 minutes following topical challenge, mice were euthanized and surgically procured conjunctivae (including bulbar through palpebral regions from both the superior and inferior areas) were placed on ice cold PBS. Single cell suspensions were prepared using standard collagenase digestion methods as previously described (Saban D R et al., 2009 Am J Transplant. March; 9(3):473-82). Briefly, conjunctivae were minced into small fragments, followed by digestion with 2 mg/ml collagenase type IV and 0.05 mg/ml DNase I (Roche, Basel, Switzerland) for 2 to 3 h at 37° C. The suspension was triturated using a syringe and filtered through a 70-μm cell strainer. Cells were thoroughly washed and resuspended in 0.5% BSA buffer, followed by an anti-FcR (CD16/CD32) blockade step as per manufacturer's instructions (BD Pharmingen). Cells were subsequently stained as per manufacturer's instructions with Alexa-647-conjugated anti-CD45 Ab (Biolegend, CA), Alexa-488-conjugated anti-CD117 (Biolegend, CA), PE-conjugated CCR3 (Biolegend, CA) or appropriate isotype controls. After 30 min, cells were washed and resuspended for subsequent acquisition using a BD LSR II flow cytometer (BD Biosciences, San Jose, Calif., USA).

Measurement of T Cell Responses to Recall Allergen Stimulation

Regional LN (cervical and submandibular) were collected and pooled from freshly euthanized mice. Single-cell suspensions were prepared and T cells were MACS sorted as described above. Enriched T cells were enumerated via trypan blue exclusion assay, and plated in round-bottom 96-wells at a concentration of $1.25 \times 10^6$/ml. Immature BMDCs prepared as described above were plated with T cells at a concentration $0.625 \times 10^6$/ml. Co-cultures were plated in triplicate wells of RPMI (10% FBS) with OVA (1 mg/ml) for up to 24 hr and restimulated with PMA/Ionomycin and Brefeldin A (Sigma Aldrich, St. Louis, USA) for up to 9 hours. Harvested supernatant was measured via ELISA for Th2 (IL-4, IL-5, and IL-13) cytokines, as per manufacturer's instructions (READY-SET-GO® ELISA kit, EBIOSCIENCE®, San Diego, USA).

RNA Isolation and Real-Time Polymerase Chain Reaction

Total RNA was isolated using TRIZOL® (INVITROGEN®) and RNEASY MICROKIT® (QIAGEN®). The first strand of complementary DNA (cDNA) was synthesized with random hexamers using SUPERSCRIPT III™ reverse transcriptase (INVITROGEN®) and quantitative real-time polymerase chain reaction was performed using TAQMAN® Universal PCR Mastermix and FAM-MGB dye-labeled predesigned primers (APPLIED BIOSYSTEMS®) for CCR7 (Mm01301785_m1), CCL19 (Mm00839967_g1), CCL21 (Mm03646971_gH), and glyceraldehydes 3-phosphate dehydrogenase (GAPDH) (Mm99999915_g1). Two microliter of cDNA was loaded in each well, and the assays were performed in duplicate. The GAPDH gene was used as the endogenous reference for each reaction. The results were analyzed by the comparative threshold cycle (CT) method and the relative expression level of each sample was expressed as fold change from naïve control.

Topical CCR7 Blockade

Wild-type (WT) C57BL/6 mice were immunized once i.p. with a 100 ul suspension containing 1 mg aluminum hydroxide (SIGMA ALDRICH®, St. Louis, USA) diluted in HBSS, 300 ng pertussis toxin (SIGMA ALDRICH®), and 100 ug ovalbumin (Sigma Aldrich). Three weeks post immunization mice were challenged topically, once daily for 4 consecutive days, with OVA (250 ug) loaded eye drops (5 ul), containing 1% monoclonal Ab (25 ug) against CCR7 or the matching isotype control (R&D Systems).

Statistical Analysis

Statistical analyses included 1-way ANOVA and Bonferroni's Multiple Comparison Test, in addition to two-tailed student's t-test. Standard error and standard deviation of the mean were calculated. A p-value <0.05 was considered statistically significant.

Figure 7A:
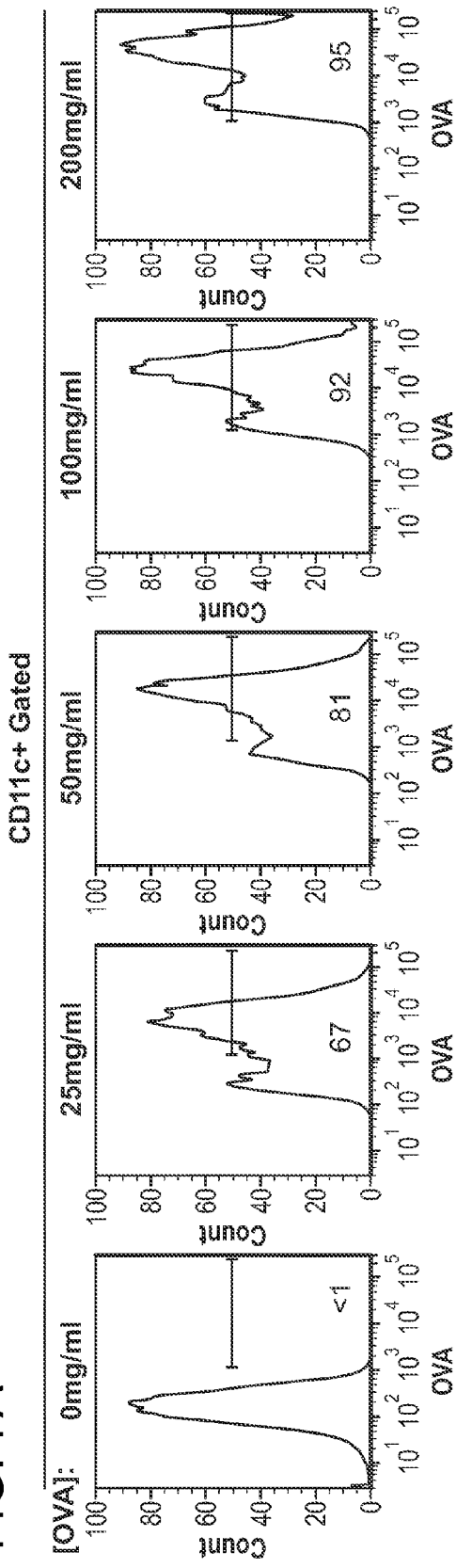
FIG. 7A is a series of cell plots showing that BMDCs efficiently capture allergen in vitro. Various concentrations of FITC-conjugated OVA were used to pulse immature BMDCs and OVA+ DCs were subsequently enumerated via FACS analysis.
Figure 7B:
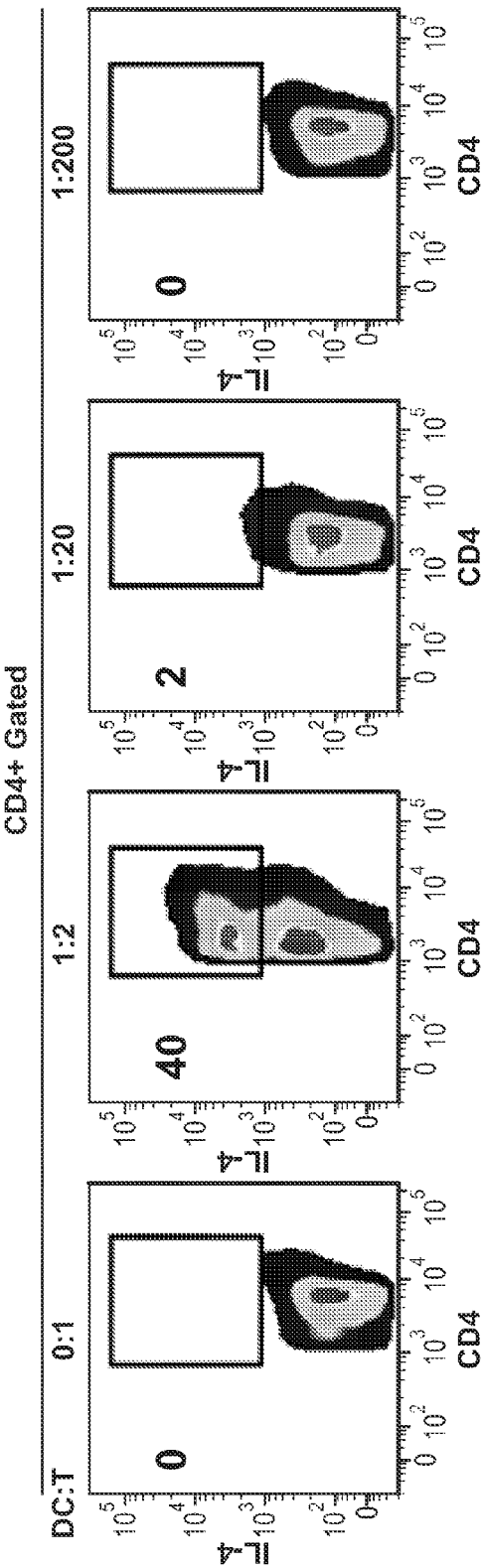
FIG. 7B is a series of cell plots showing allergen-laden BMDCs expand Th2 cells in vitro. MACS sorted T cells originating from OVA/Alum-primed mice were co-cultured at various concentrations with BMDCs in the presence of OVA. Consequent expansion of Th2 cells were enumerated via FACS analysis of CD4+ IL-4+ T cells from respective cultures.

DCs from the Allergen Exposed Ocular Surface, Confer Upregulated CCR7 Expression in Lymphoid Tissues It was investigated whether CCR7 expression by DCs from allergen-exposed tissue-sites (i.e., conjunctiva), plays a role in the mobilization of these cells to the lymphoid compartment in an allergic immune response. Exogenous eGFP+ DCs was locally administered via subconjunctival (SCJ) injection into wild-type (WT) mice Immediately thereafter, eye drops of Texas-Red conjugated OVA were utilized, thereby allowing the identification of migrating allergen-laden DCs (i.e., Texas-Red+ eGFP+) in host LN. Exogenous DCs used here were derived from bone marrow cells of syngeneic eGFP+ hosts and cultivated via standard ex vivo procedures (Lutz M B et al., 1999 J Immunol Methods. February 1; 223(1):77-92). Bone marrow derived DCs were well-suited for the line of investigation, as use of these cells in a similar manner has been previously been described (Kuipers H et al., 2009 J Leukoc Biol. January; 85(1):64-70), and also these DCs were highly efficient at capturing OVA in vitro, as well as effective at stimulating Th2 expansion in vitro (FIG. 7A and FIG. 7B).

Figure 1A:
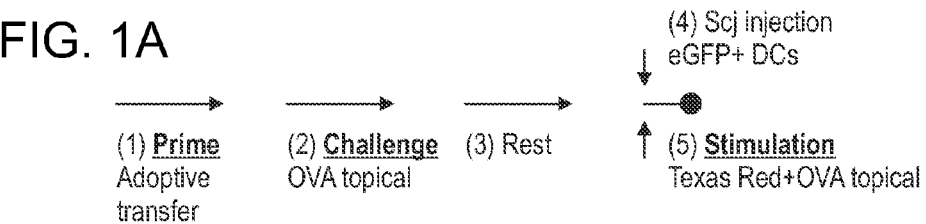
FIG. 1A is a schematic showing magnetic-activated cell sorting (MACS)-sorted T cells harvested from OVA/Alum-primed mice were adoptively transferred into naïve hosts (1); subsequently, hosts were challenged once daily for at least 10 days via topical instillation of ovalbumin (OVA)-loaded drops to one eye (2); mice were then rested for several weeks (3); and subsequently subconjunctivally (SCJ)-injected with enhanced green fluorescent protein (eGFP)+ DCs (4); followed by immediate stimulation with TEXAS RED®-conjugated OVA eye drops (5).
Figure 1B:
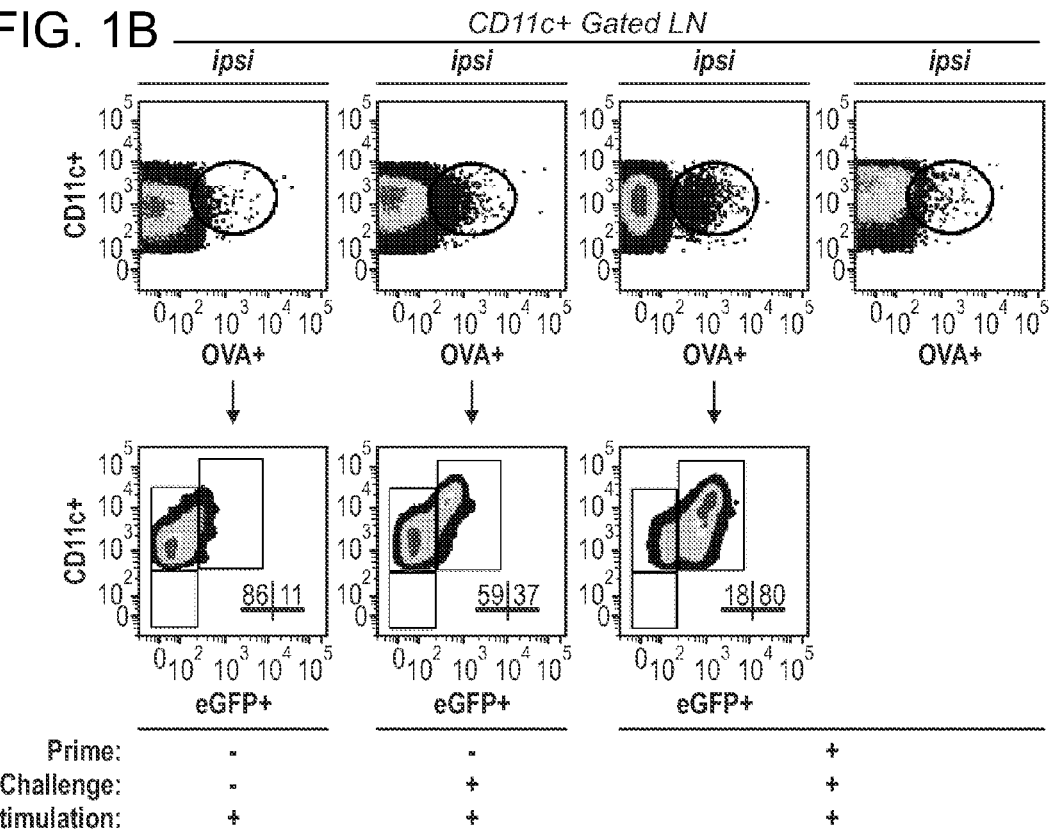
FIG. 1B is a series of cell sorting plots showing the identification of SCJ-injected eGFP+ DCs that are OVA+ in ipsilateral lymph node (LN) of AC-induced hosts. Fluorescence-activated cell sorting (FACS) analysis of DCs was performed on ipsilateral (ipsi) and contralateral (contra) LNs. OVA+ CD11c+ cells were gated on and subsequently eGFP+ CD11c+ frequencies were enumerated.

Mice used in this experiment were adoptively transferred with OVA/Alum-primed T cells and subsequently challenged via a series of instillations with OVA-loaded eye drops to induce AC (FIG. 1A). Mice were subsequently rested for several weeks, and then received SCJ injection with eGFP+ DCs plus immediately stimulated with conjugated OVA eye drops (FIG. 1A), thereby mimicking initiation of an allergic reaction. Regional LN (i.e., cervical and submandibular LN) including the active ipsilateral node and the presumably inactive contralateral node were then harvested for FACS analyses. This was also carried out in non AC-induced control mice as well, which are indicated in FIG. 1B. Data in FIG. 1 represent analyses at 4 hr post challenge, since conjugated OVA was less detectable at later time-points, including 12 and 24 hr. mRNA analysis was also conducted on conjunctival tissues of immunized subsequent to challenge and a fold increase of 1.870±0.2660 in CCR7 (p=0.04), 1.714±0.1527 in CCL19 (p=0.001), but not in CCL21 (p=0.8) relative to naive conjunctiva was observed.

Figure 1C:
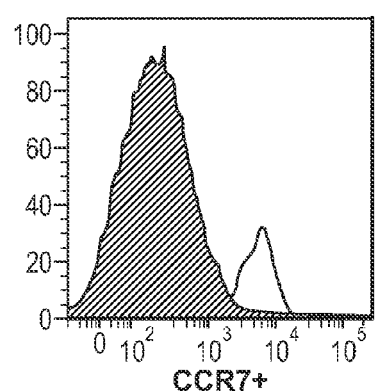
FIG. 1C is a cell sorting plot and a bar chart showing SCJ-injected eGFP+ DCs that are OVA+ confer increased CCR7 expression in LN of AC-induced mice. By flow cytometry and reverse transcription polymerase chain reaction (RT-PCR), in vitro generated eGFP+ DCs prior SCJ injection were directly compared to CD11c+ eGFP+ OVA+ DCs found in ipsi LN of AC-induced mice. Each experimental group represents an n=3 hosts, and data are representative of multiple independent experiments.
Figure 1C:
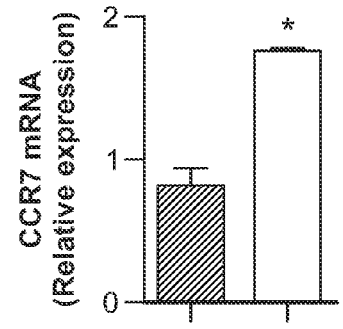
Figure 8A:
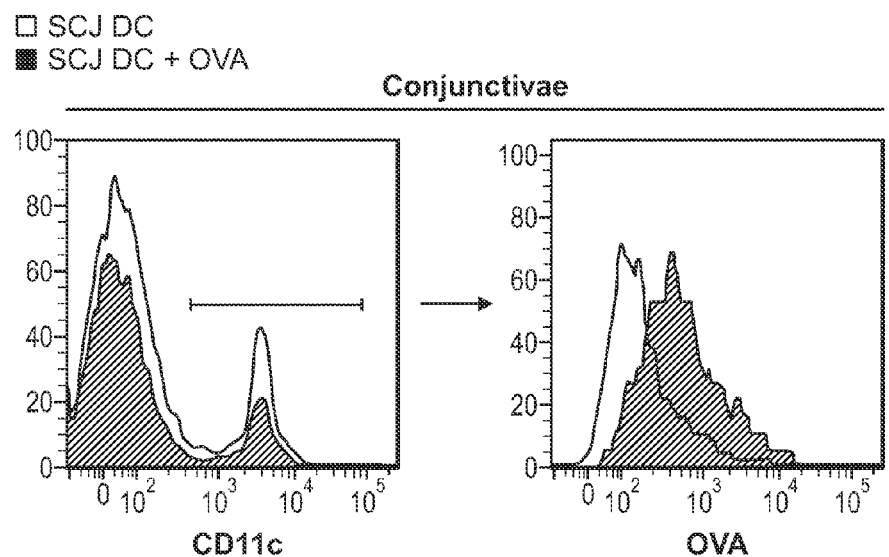
FIG. 8A is cell plot showing SCJ injected BMDCs capture allergen from the ocular surface. Mice adoptively transferred with OVA/Alum-primed T cells, were instilled with (or without) FITC-conjugated OVA eye drops immediately following SCJ injection of exogenous BMDCs.
Figure 8B:
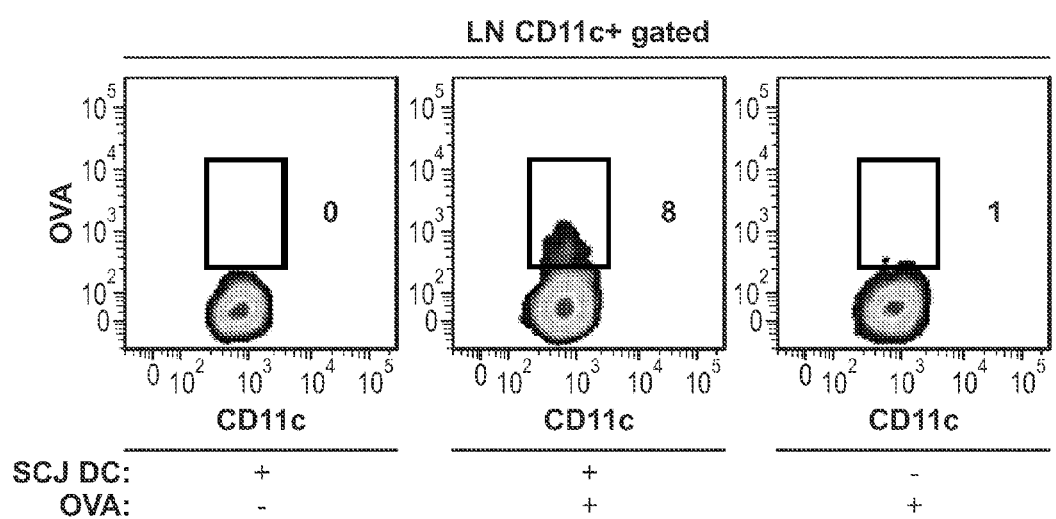
FIG. 8B is a cell plot showing SCJ injected BMDCs which capture allergen from the ocular surface, mobilize to the LN. Adoptively transferred mice were SCJ injected with BMDCs (or sham HBSS) and immediately challenged with FITC-conjugated OVA eye drops (or sham PBS) as indicated. Ipsilateral LN were FACS analyzed for CD11c+ OVA+ frequencies. Contralateral controls were also assessed.

In the LN, a very clear OVA+ CD11c+ population unique to the ipsilateral LN of AC-induced mice was detected (FIG. 1B). This was in contrast to a marginal population of OVA+ CD11c+ DCs observed in the contralateral LN of these mice (FIG. 1B), and similarly observed in LN of both groups of non AC-induced controls (FIG. 1B). AC-induced recipients of topical conjugated-OVA stimulation but without SCJ injected DCs were also examined; however, the frequency of OVA+ DCs was 8-fold lower than in similar mice with SCJ injected DCs and topical OVA stimulation (FIG. 8A and FIG. 8B). This verified the mobilization of SCJ injected DCs to local ipsilateral LN in the model. Furthermore, in AC-induced mice recipients that were SCJ injected with eGFP+ DCs and stimulated with topical OVA, nearly 80% were eGFP+ within the OVA+ CD11c+ population (FIG. 1B). Strikingly, this was 2-fold higher than the frequency of eGFP+ DCs found in the ipsilateral LN of non AC-induced mice that received equivalent OVA topical challenges; and 8-fold higher than in non AC-induced mice which did not receive OVA topical challenges (FIG. 1B). Lastly, nearly all eGFP+ DCs found in ipsilateral LN of AC-induced mice were CCR7+(FIG. 1C), and these levels were clearly increased relative to their original expression levels seen in vitro prior to SCJ injection (FIG. 1C). Taken together, these data suggest that in AC-induced mice, allergen-laden DCs mobilized to regional LN confer increased CCR7 expression.

DCs from the Ocular Surface Mount Th2 Responses in a CCR7-Dependent Fashion

The results described above indicate that upregulated CCR7 by allergen-laden DCs is associated with optimal mobilization of these cells to lymphoid tissues in an allergic response. However, once in the LN, whether these DCs are relevant in stimulating Th2 remains unknown. To address this, in vitro recall (i.e., OVA) stimulation assays of T cells isolated from ipsilateral LN of AC-induced mice were performed. Furthermore, to allow the assessment of the role on Th2 responses of CCR7 expression by DCs from allergen exposed sites, T cells for these experiments were harvested from AC-induced mice influenced by SCJ injection of WT vs. CCR7 knockout (−/−) DCs. A similar approach with injected mast cells in AC was reported by Fukeda et al (Fukuda K et al., 2009 J Allergy Clin Immunol. October; 124(4):827-33), as well as injection of exogenous DCs previously described by Lambrecht et al and others in the allergic asthma model (Lambrecht B N et al., 2000 J Clin Invest. August; 106(4):551-559; Lambrecht B N et al., 2000 J Immunol. March 15; 164(6):2937-46; Sung S et al., 2001 J Immunol. January 15; 166(2):1261-71; Kuipers H et al., 2009 J Leukoc Biol. January; 85(1):64-70).

Figure 2A:
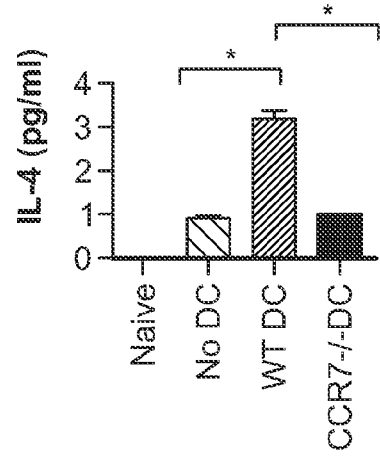
FIG. 2A shows the results of ELISA for IL-4.
Figure 2B:
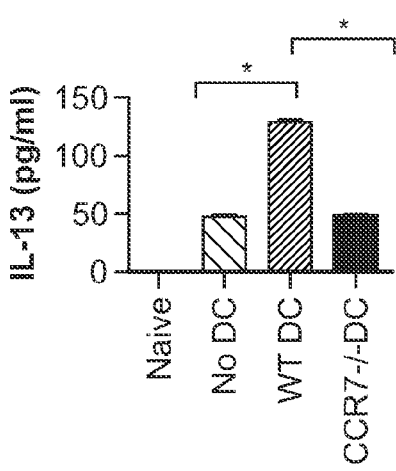
FIG. 2B shows the results of ELISA for IL-13.
Figure 2C:
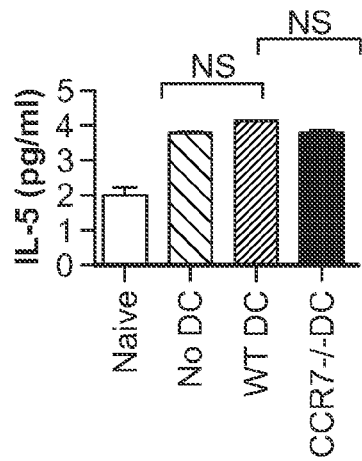
FIG. 2C shows the results of ELISA for IL-5. Data are derived from an n=5 hosts per group. Each figure represents multiple independent experiments. (*p<0.05)

Mice were adoptively transferred with OVA/Alum-primed T cells, shortly thereafter were SCJ injected with WT vs. CCR7−/− DCs, and then immediately challenged with instillations of OVA-loaded eye drops to induce AC. MACS sorted T cells from ipsilateral LN were then restimulated in vitro to OVA, and ELISA was used to measure Th2 cytokine levels (e.g., IL-4, IL-5 and IL13). Using this system, no significant differences in IL-5 levels amongst the experimental groups (FIG. 2) was detected. However, augmented levels of IL-4 and IL-13 were observed in T cells isolated from AC-induced mice SCJ injected with WT DCs (FIG. 2A and FIG. 2B). Augmentation was completely reversed in AC-induced mice that received CCR7−/− DCs, as IL-4 and IL-13 returned to control levels; i.e., AC-induced mice which did not receive SCJ injected DCs (FIG. 2A and FIG. 2B).

Figure 3:
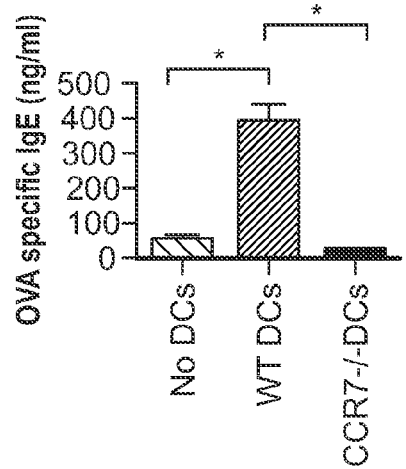
FIG. 3 is a bar chart demonstrating that the expression of CCR7 by DCs from the ocular surface is necessary for contribution to consequent IgE production. WT DCs, CCR7−/− DCs, or no SCJ injection was administered into mice following adoptively transfer with OVA/Alum-primed T cells. Blood was collected from hosts after at least 10 days of once daily OVA topical challenges. Sera was isolated and measured for OVA-specific IgE. Data are derived from an n=5 hosts per group. Each figure represents multiple independent experiments. (*p<0.05)

OVA specific IgE in the sera of AC-induced mice SCJ injected with WT vs. CCR7−/− DCs was also assessed, as Th2 cytokines (including IL-13 and IL-4) are required for consequent plasma cell synthesis of IgE. Control AC-induced mice (that were not SCJ injected with DCs) had marginal to low levels of OVA specific IgE, while these levels were augmented nearly 10-fold in mice that were SCJ injected with WT DCs (FIG. 3). However, this augmentation was completely reversed (to levels seen in controls) when AC-induced mice were SCJ injected instead with CCR7−/− DCs (FIG. 3), suggesting that DCs from allergen exposed sites mount allergen Th2 responses in a CCR7-dependent fashion.

Figure 4A:
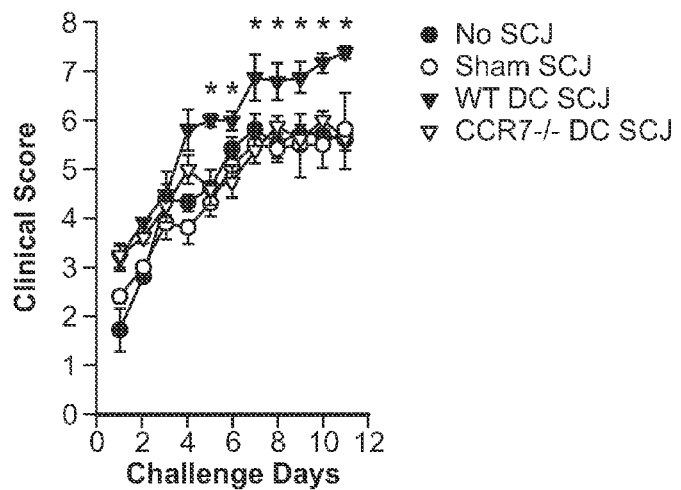
FIG. 4A is a line graph showing that SCJ injection of CCR7−/− DCs results in impaired onset and progression of AC clinical signs. WT DCs, CCR7−/− DCs, sham Hank's buffered salt solution (HBSS), or no SCJ injection was administered into mice following adoptive transfer with OVA/Alum-primed T cells. All mice were challenged topically with OVA eye drops once daily for at least 10 days and scored biomicroscopically 20 minutes post challenge for clinical signs (e.g., redness [R], chemosis [Ch], tearing/discharge [T], and lid swelling [LS]).
Figure 4B:
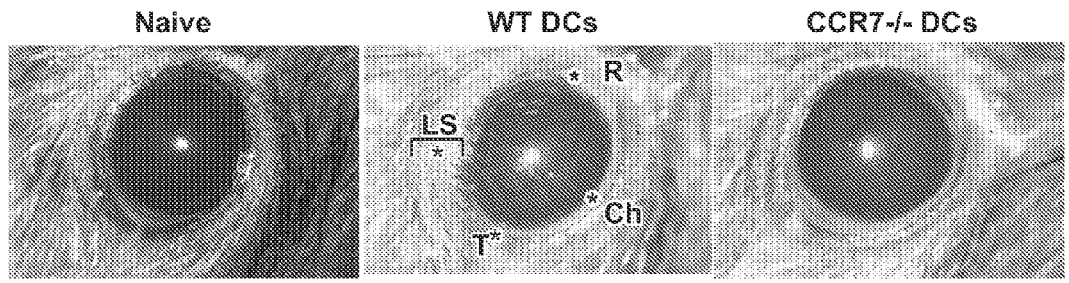
FIG. 4B is a series of photomicrographs showing representative clinical photographs of mice SCJ administered with WT versus CCR7−/− DCs on day 10 of topical challenge.

DCs from the Ocular Surface Contribute Via CCR7 to Elicitation of Allergic Conjunctivitis Th2 cytokines are important in eosinophil degranulation and allergen-specific IgE is important in mast cell degranulation, which causes an allergic reaction. Based on this understanding, the suggested CCR7-dependent mechanism by which DCs mounts a Th2 response, and consequent synthesis of IgE, would therefore be expected to lead to an allergic reaction as well. Thus, to determine if this may be the case, adoptively transferred mice received an SCJ injection of WT or CCR7−/− DCs, and the onset and progression of AC clinical signs to topical OVA challenges were examined Challenges were administered once daily for more than 10 days and scored twenty minutes post challenge as previously described (Reyes N J, et al., 2010 Int Immunol. August; 22(8):627-36). SCJ injection of WT DCs to adoptively transferred mice significantly augmented AC clinical scores as early as day 5 of topical challenge (p<0.05), relative to adoptively transferred mice that received no SCJ injection or sham PBS SCJ injection (FIG. 4A and FIG. 4B). However, this augmentation was completely abrogated when OVA challenges were instilled on adoptively transferred hosts that were SCJ injected with CCR7−/− DCs (FIG. 4A and FIG. 4B), indicating that DCs from allergen exposed sites contribute to an allergic reaction in a CCR7-dependent manner.

Figure 4C:
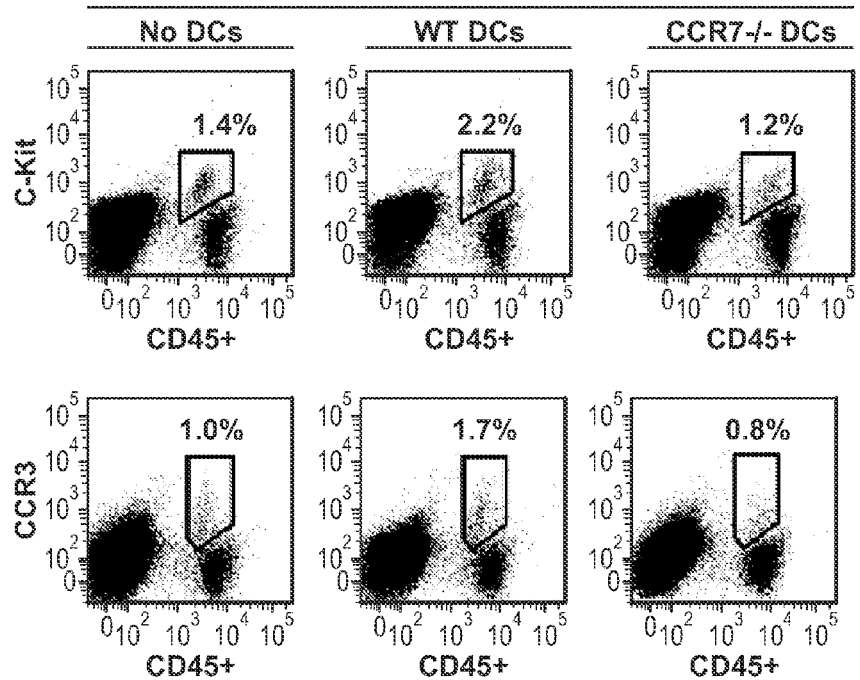
FIG. 4C is a series of cell plots showing that impaired AC clinical scores conferred by CCR7−/− DCs are associated with decreased number of conjunctival mast cells and eosinophils. Conjunctivae were collected from AC-induced mice after at least 10 days of once daily OVA topical challenges. Tissue was prepared into single-cell suspensions and FACS analysis was performed for mast cells (CD45+ c-Kit+) and eosinophils (CD45+ CCR3+). Data are derived from n=4 to 5 hosts per group, and figure represents multiple independent experiments.

Mast cells and eosinophils were also enumerated in the conjunctivae of AC-induced mice influenced by SCJ injection of WT vs. CCR7−/− DCs, since allergic reactivity can correlate with increased infiltration of mast cells and eosinophils. FACS analysis was therefore performed on collagenase-digested conjunctivae of AC-induced mice topically challenged for at least 10 days (a time point consistent with peak AC clinical signs). Mast cells were discerned by their CD45+ c-Kit+ phenotype, as confirmed by the P815 mastocytoma cell line which were ~100% CD45+ c-Kit+. Baseline frequencies of mast cells were <0.3% in the normal conjunctivae, whereas peak AC clinical signs increased to 1.4% CD45+ c-Kit+ (FIG. 4C). In AC-induced mice SCJ injected with WT DCs, this was increased to 2.2% CD45+ c-Kit+ (FIG. 4C), thereby corroborating the augmented scores seen clinically in these mice. However, this increase was completely abrogated to 1.2% CD45+ c-Kit+ in AC-induced mice SCJ injected with CCR7−/− DCs (FIG. 4C).

This trend was consistent when enumerating eosinophils (CD45+ CCR3+) as well, since AC-induced mice recipient of SCJ injected WT DCs had increased eosinophils, whereas this increase was completely reversed in mice recipient of SCJ injected CCR7−/− DCs (FIG. 4C).

Subconjunctival Injection with Wild-Type, but not CCR7−/−, DCs Augments Allergic Immune Responses in CCR7−/− Hosts It was next determined whether CCR7-sufficient endogenous DCs can significantly influence the effect seen by SCJ injected WT or CCR7−/− DCs in the AC model described herein. This was accomplished by using CCR7−/− hosts (thereby consisting of CCR7−/− endogenous DCs) and compared the effect of SCJ injected WT vs. CCR7−/− DCs on allergic immunity in the AC model described herein. Mice were adoptively transferred with OVA/Alum-primed T cells (WT), followed by SCJ injection of DCs and immediate topical challenge. Mice were challenged once daily for more than 10 days and clinically scored. Conjunctivae were also harvested for FACS enumeration of mast cells and eosinophils, and blood was collected for OVA-specific IgE quantitation of sera via ELISA.

Figure 9:
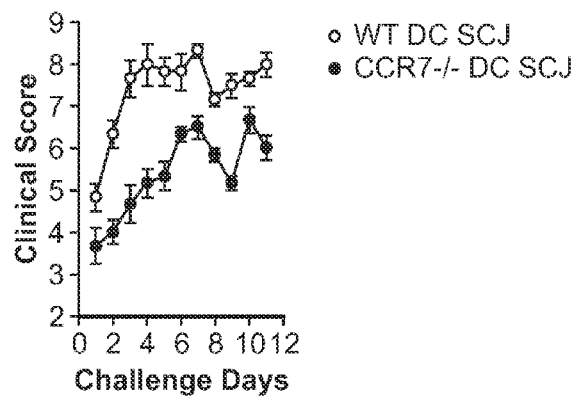
FIG. 9 is a line graph showing SCJ injected WT, but not CCR7−/−, DCs in hosts adoptively transferred with primed OTII T cells mount an allergic reaction in CCR7-deficient hosts. SCJ injection of WT DCs or CCR7−/− DCs was administered into mice (n=5/group) following adoptively transfer with OTII OVA/Alum-primed T cells. All mice were challenged topically with OVA eye drops once daily for at least 10 days and scored biomicroscopically 20 minutes post challenge for AC clinical signs.

In CCR7−/− hosts, SCJ injection of WT DCs augmented clinical scores as early as day 1 relative to control CCR7−/− mice that were not SCJ injected with DCs (FIG. 5A). This was not the case in AC-induced CCR7−/− mice that were SCJ injected with CCR7−/− DCs, as clinical scores were only slightly and mostly insignificantly elevated over control mice (FIG. 5A). In an additional experiment, OVA/Alum-primed OTII T cells were adoptively transferred into CCR7−/− hosts (as performed in Hintzen G et al., 2006 J Immunol. November 15; 177(10):7346-54), and again found that SCJ injection of WT DCs, but not CCR7−/− DCs, augmented clinical signs in AC (FIG. 9). In an another experiment, DCs mobilized by ocular surface allergen upregulated CCR7 in lymphoid tissues.

Quantitation of OVA-specific IgE similarly showed augmented levels in SCJ injected mice with WT DCs, relative to control mice that were not SCJ injected (FIG. 5B), whereas in SCJ injected mice with CCR7−/− DCs, levels were not augmented and similar to that of the control (FIG. 5B). In line with this, mast cell (CD45+ c-Kit+) and eosinophil (CD45+ CCR3+) numbers were augmented only in SCJ injected mice with WT DCs, relative to control (FIG. 5C), whereas this augmentation was absent in SCJ injected mice with CCR7−/− DCs (FIG. 5C). Thus, SCJ injected wild-type, but not CCR7−/−, DCs augments allergic immune responses in CCR7−/− hosts.

Figure 6A:
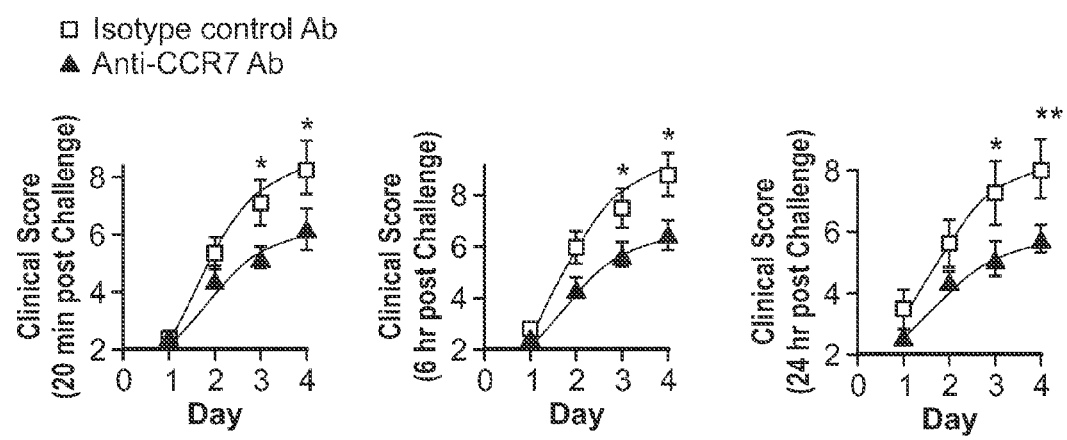
FIG. 6A is a line graph showing that mice were scored for clinical signs biomicroscopically at 20 minutes, 6 hr, and 24 hr post challenge.
Figure 6B:
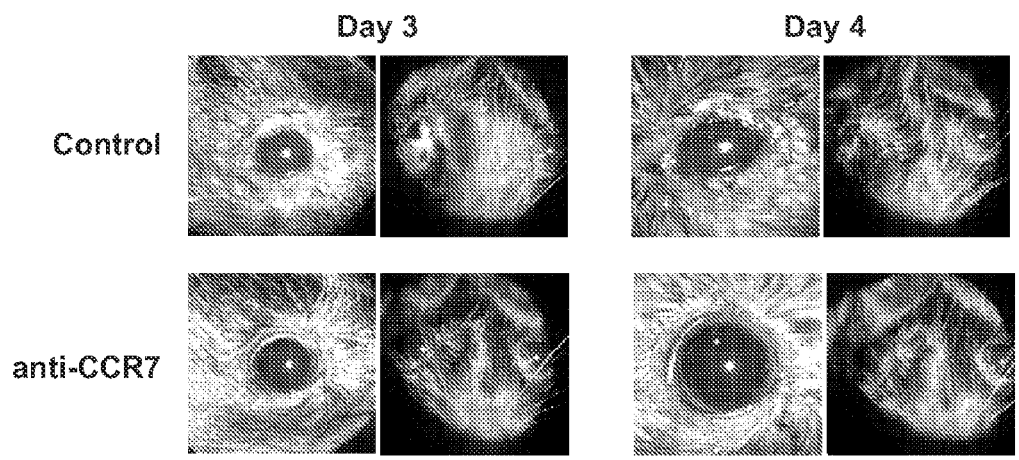
FIG. 6B is a series of photomicrographs showing representative clinical images on challenge day 3 and day 4. Data are derived from n=5 hosts per group. Each figure represents multiple independent experiments. ($*p<0.05$)

Examination of Topical Administration of Anti-CCR7 Ab Blockade in Allergic Conjunctivitis Because CCR7 deficient DCs at the level of the ocular surface demonstrated an impaired capacity to trigger allergic immune responses to OVA instilled eye drops, it was determined whether a similar clinical effect could be demonstrated with topically administered anti-CCR7 antibody in actively immunized mice. To test this, mice were immunized against OVA and then rested for 3 weeks. Mice were subsequently challenged once daily for 4 days with OVA eye drops containing either 1% anti-CCR7 Ab or isotype control Ab (FIG. 6). Clinical scores were determined at 20 minutes, 6 hrs, and 24 hrs post challenge (FIG. 6). All 3 of these time points post challenge, anti-CCR7 Ab administration significantly decreased clinical scores, particularly to challenges given on days 3 ($p<0.05$) and 4 ($p<0.05$) (FIG. 6A and FIG. 6B).

The sequence of a mouse C—C chemokine receptor type 7 precursor is provided in NCBI Reference Sequence: NP_031745.2 (GI:116268121), incorporated herein by reference. A neutralizing antibody that detects mouse CCR7 (monoclonal Rat IgG$_{2A}$ clone #4B12) is publically available through R&D SYSTEMS® (catalog Number: MAB3477). The immunogen for the monoclonal Rat IgG$_{2A}$ clone #4B12 antibody was RBC-2H3 cells expressing mouse CCR7 (GENBANK Accession Number NP_031745.2 (GI: 116268121), incorporated herein by reference).

The Gene ID of human CCR7 is 1236, incorporated herein by reference. The nucleic acid sequence of human CCR7 is provided in GENBANK Accession Number NM_001838.3 (GI:299473754), incorporated herein by reference. The amino acid sequence of human CCR7 is provided in GENBANK Accession Number NP_001829.1 (GI: 4502641), incorporated herein by reference.

A neutralizing antibody that detects human CCR7 (monoclonal mouse IgG$_{2A}$ clone #150503) is publically available through R&D SYSTEMS® (catalog Number: MAB197). An anti-Human CD197 (CCR7) purified antibody (clone: CCR7.6B3) is publically available through EBIOSCIENCE® (catalog numbers: 14-9977-80 and 14-9977-82). The CCR7.6B3 monoclonal antibody reacts with human CCR7, also known as EBI-1 and CD197. An ALEXAFLUOR® 647 Rat anti-Human CD197 (CCR7) antibody (clone 3D12) is publically available through BD PHARMINGEN™ (material number 557734). The monoclonal antibody 3D12 reacts with the human CC chemokine receptor, CCR7. An APC anti-human CD197 (CCR7) antibody (clone G043H7) is publically available through BIOLGEND® (catalogue number 353213 and 353214).

Additional anti-CCR7 antibodies are set forth in U.S. Pat. No. 8,066,996, incorporated herein by reference. Various immunoassays, such as competitive binding assays and immunoradiometric assays can be used to identify antibodies having the desired specificity. Numerous protocols for these assays are well known in the art. See, e.g., U.S. Pat. No. 8,066,996 at column 7, lines 32-44, incorporated herein by reference.

The current study has uncovered a strategy, involving topical administration of CCR7 antagonist, which the results indicate can potentially be applied clinically for management of allergic conjunctivitis. The efficacy of this blockade was based on an important role for CCR7 expression by ocular surface DCs in promoting allergic immune responses. These findings to some extent are in contrast to previous work describing a role for DC expression of CCR7 in the cornea (Jin Y et al., 2010 Invest Ophthalmol Vis Sci. February; 51(2):816-21), and also shown in the lung (Sánchez-Sánchez N et al., 2006 J Immunol. May 1; 176(9): 5153-9; Yamashita N et al., 2006 Allergy Clin Immunol. May; 117(5):1040-6; Grinnan D et al., J Allergy Clin Immunol. 2006 December; 118(6):1234-41; Hintzen G et al., 2006 J Immunol. November 15; 177(10):7346-54) in the suppression of immunity via tolerance. These potentially opposing roles (i.e., promoting versus modulating immunity) highlight the notion that CCR7 function on DCs has various facets, and thereby underscores the need for studies such as these to continue to understand its important function in controlling immune responses (Sánchez-Sánchez N et al., 2006 J Immunol. May 1; 176(9):5153-9).

The role of CCR7 in promoting AC immunopathogenesis was revealed in an experimental murine model in which WT mice were engrafted with exogenous WT vs. CCR7−/− DCs into the conjunctiva. This approach is in contrast to inducing allergy in CCR7−/− mice or plt mice (Yamashita N et al., 2006 J Allergy Clin Immunol. May; 117(5):1040-6; Grinnan D et al., 2006 J Allergy Clin Immunol. December; 118(6):

1234-41; Hintzen G et al., 2006 J Immunol. November 15; 177(10):7346-54; i.e., deficient in lymphoid CCL19 and CCL21) to address this, as (in addition to DCs) lymphocytes too express CCR7. The approach enabled a focus on the function of the CCR7-CCL19/CCL21 axis on DCs from the ocular surface. Furthermore, exogenous DCs were not allergen pulsed prior to engraftment and which akin to endogenous tissue DCs, thus had to capture allergen from topical exposure. This is distinguishable from seminal work done in allergic airway hypersensitivity, whereby exogenous DCs were pulsed with allergen prior to intratracheal injection (Lambrecht B N et al., 2000 J Clin Invest. August; 106(4): 551-559; Lambrecht B N et al., 2000 J Immunol. March 15; 164(6):2937-46; Sung S et al., 2001 J Immunol. January 15; 166(2):1261-71; Kuipers H et al., 2009 J Leukoc Biol. January; 85(1):64-70). Hence, the model described herein allowed for the determination of the effect of deleting CCR7 in DCs at the ocular surface. As described herein, a stark impairment in AC immunopathogenesis was observed.

Several pieces of evidence allowed making the identification that the CCR7-CCL19/CCL21 axis plays a key role in mobilizing ocular surface DCs to generate an allergic immune response. This is supported by the observation that nearly all SCJ injected DCs (eGFP+) that had captured topically instilled OVA (TEXAS RED+®) conferred very strong upregulation of CCR7+ expression in the LN of AC-induced mice. Furthermore, mobilization of SCJ injected eGFP+ DCs to LN was optimal in mice that were both allergen primed and subsequently allergen challenged (both of which are required to induce an allergic reaction in AC), thereby implicating a role for an allergic reaction in triggering DC mobilization. In contrast, only marginal mobilization of SCJ injected eGFP+ DCs to LN was found in non AC-induced mice (i.e. without an allergic reaction), including mice that were primed but not challenged; or challenged but not primed.

These series of experiments, in addition to demonstrating optimal mobilization of DCs from the site of allergen exposure to LN, also signified a potentially important difference by which allergen is processed in allergy. The data suggest that in AC-induced mice, allergen is captured and presumably presented by DCs from the ocular surface. In contrast, in non AC-induced mice, 'free' form allergen in lymphatic drainage (Pape K A et al., 2007 Immunity. April; 26(4):491-502; Roozendaal R et al., Immunity. 2009, 30:264-76) is likely captured (and presumably presented) mostly by other DCs (eGFP-), such as LN resident DCs. This is supported by the observation that <40% of OVA+ DCs were eGFP+ in LN of non AC-induced mice; whereas 80% of allergen-laden DCs were eGFP+ in LN of AC-induced mice. The significance of this may be related to Hawiger et al, who reported that resident LN DCs (in contrast to mobilized tissue DCs) present Ag in a tolerogenic fashion (Hawiger D et al., 2001 J Exp Med. September 17; 194(6):769-79).

In addition to facilitating entry into regional lymphatics and LN, CCR7 could also play an important role in directing allergen-laden DCs to the T cell-rich paracortex region of the LN in allergy. Indeed, this process is made possible by the CCL21 gradient established by HEV located in the paracortex, and would promote engagement and activation of T cells by DCs (Sozzani S et al., 1998 J Immunol. August 1; 161(3):1083-6; Dieu M C et al., 1998 J Exp Med. July 20; 188(2):373-86; Gunn M D et al., 1999 J Exp Med. February 1; 189(3):451-60; Saeki H et al., 1999 J Immunol. March 1; 162(5):2472-5). Consistent with this, in vitro stimulated (with recall allergen) T cells isolated from AC-induced mice that were SCJ injected with WT DCs, showed a significantly enhanced Th2 reaction—as indicated by IL-13 and IL-4 production (but not IL-5). This augmented Th2 reactivity was completely abrogated in T cells isolated from AC-induced mice SCJ injected with CCR7-/- DCs. Thus, this finding, i.e., DCs which capture allergen from the ocular surface lead to Th2 responses in a CCR7-dependent fashion, is likely contributed in part by CCR7-mediated trafficking of DCs to the paracortex, to in turn promote Th2.

Consistent with this, the additional findings indicate that production of allergen-specific IgE is also led to by DCs from ocular surface in a CCR7-dependent fashion. This is supportive evidence because differentiation of Ag-experienced B cells, a process that is required for development of IgE synthesizing plasma cells, is mostly driven by Th2 cytokines (Emson C L et al., 1998 J Exp Med. July 20; 188(2):399-404). Thus, as seen in AC-induced mice that were SCJ injected with WT DCs, augmented Th2 responses could be expected to have caused the observed increase in allergen-specific IgE production (via promoting differentiation of allergen-experienced B cells). Furthermore, consistent with Roozendaal et al and others, B cells likely captured allergen (a prerequisite for their differentiation) in the 'free' form within lymphatic drainage (Roozendaal R et al., 2009 Immunity., 30:264-76; Hawiger D et al., 2001 J Exp Med. September 17; 194(6):769-79).

The totality of the findings, indicating that DCs from the ocular surface mount allergic immune responses in a CCR7-dependent fashion, is not in conflict with the understanding that the CCL19/21-CCR7 axis can also be involved with mediating allergen-induced tolerance (Yamashita N et al., 2006 J Allergy Clin Immunol. May; 117(5):1040-6; Grinnan D et al., 2006 J Allergy Clin Immunol. December; 118(6): 1234-41; Hintzen G et al., 2006 J Immunol. November 15; 177(10):7346-54). Indeed, CCR7 expressed by different immune cells is known to exert different effects (Sánchez-Sánchez N et al., 2006 J Immunol. May 1; 176(9):5153-9). For instance, CD4+ CD25+ FoxP3+ Treg expression of CCR7 is known to facilitate the trafficking of these cells into LN for consequent suppression of effector T cell expansion (Schneider M A, et al., 2007 J Exp Med. April 16; 204(4): 735-45). Also relevant are reports that implicate an impaired Treg compartment in plt and CCR7-/- mice (Gunn M D et al., 1999 J Exp Med. February 1; 189(3):451-60; Schneider M A, et al., 2007 J Exp Med. April 16; 204(4):735-45), which thereby could have contributed to impaired tolerance induction to allergen seen in CCR7-/- mice by Hintzen et al (Hintzen G et al., 2006 J Immunol. November 15; 177(10):7346-54), or exaggerated allergen responses observed by Yamashita et al and Grinnan et al in plt mice (Yamashita N et al., 2006 J Allergy Clin Immunol. May; 117(5):1040-6; Grinnan D et al., 2006 J Allergy Clin Immunol. December; 118(6):1234-41). Likewise reflected in the study, SCJ injection of WT DCs led to significant augmentation of AC clinical signs in CCR7-/- mice as early as day 1 of allergen challenge, but not until day 5 in WT hosts. Thus, it is very important to consider the specific immune cell population that is being affected when examining the CCR7-CCL19/21 axis in any immune response (Sánchez-Sánchez N et al., 2006 J Immunol. May 1; 176(9):5153-9).

In summary, it is concluded that blockade of CCR7 at the level of the ocular surface inhibits the immunopathogenesis of AC. The data indicate that blockade interferes with the mobilization of allergen-laden DCs to regional LN and their trafficking specifically to the paracortex for engagement of cognate T cells. This, in turn, inhibits Th2 reactivity and consequent synthesis of IgE, both of which contribute to the allergic reaction, as indicated by this AC model. This is consistent with Hammad et al's report that CCR7 expression by DCs promotes allergic pulmonary inflammation (Hammad H et al., 2002 J Immunol. August; 169(3):1524-34), and such convergent findings in the both ocular surface and lung thus give further credence to the importance of CCR7 expression by DCs in eliciting allergic immunity.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. GENBANK and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating an inflammatory condition of the ocular surface, said method comprising administering to the eye of a subject in need thereof an ophthalmic formulation comprising an effective amount of one or more C—C chemokine receptor type 7 (CCR7) antibodies.

2. The method of claim 1, wherein the concentration of one or more CCR7 antibodies is from 0.10% to 2.0% (w/v).

3. The method of claim 1, wherein the condition is an allergic condition of the ocular surface.

4. The method of claim 1, wherein the condition is selected from the group consisting of conjunctivitis, hay fever conjunctivitis, seasonal allergic conjunctivitis, atopic conjunctivitis, vernal conjunctivitis, keratoconjunctivitis, atopic keratoconjunctivitis, vernal keratoconjunctivitis, allergic rhinoconjunctivitis, and giant papillary conjunctivitis.

5. The method of claim 1, wherein the condition is selected from the group consisting of ocular inflammation, uveitis, scleritis, keratitis, retinitis, iritis, uveoretinitis, uveoscleritis, conjunctivitis, episcleritis, optic neuritis, retrobulbar neuritis, blepharitis, Mooren's ulcer and inflammatory ocular manifestations in allergies.

6. The method of claim 1, wherein the formulation further comprises one or more tear substitutes.

7. The method of claim 1, wherein the formulation further comprises an ophthalmic lubricant.

8. The method of claim 1, wherein the subject is human.

9. The method of claim 4, wherein the conjunctivitis comprises allergic conjunctivitis.

10. The method of claim 9, wherein the allergic conjunctivitis comprises perennial allergic conjunctivitis.

* * * * *

SEQUENCE LISTING

<160> NUMBER OF SEQ ID NOS: 8

<210> SEQ ID NO 1
<211> LENGTH: 98
<212> TYPE: PRT
<213> ORGANISM: Homo sapiens

<400> SEQUENCE: 1

```
Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser
```

<210> SEQ ID NO 2
<211> LENGTH: 134
<212> TYPE: PRT
<213> ORGANISM: Homo sapiens

<400> SEQUENCE: 2

```
Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
```

```
                100                 105                 110
Gly Lys Lys Gly Lys Gly Ser Lys Gly Cys Lys Arg Thr Glu Arg Ser
        115                 120                 125

Gln Thr Pro Lys Gly Pro
        130
```

<210> SEQ ID NO 3
<211> LENGTH: 9
<212> TYPE: PRT
<213> ORGANISM: Artificial Sequence
<220> FEATURE:
<223> OTHER INFORMATION: CCL19 N-Terminal

<400> SEQUENCE: 3

```
Gly Ala Asn Asp Ala Glu Asp Cys Cys
1               5
```

<210> SEQ ID NO 4
<211> LENGTH: 8
<212> TYPE: PRT
<213> ORGANISM: Artificial Sequence
<220> FEATURE:
<223> OTHER INFORMATION: CCL19 (2-83) N-Terminal

<400> SEQUENCE: 4

```
Ala Asn Asp Ala Glu Asp Cys Cys
1               5
```

<210> SEQ ID NO 5
<211> LENGTH: 7
<212> TYPE: PRT
<213> ORGANISM: Artificial Sequence
<220> FEATURE:
<223> OTHER INFORMATION: CCL19 (3-83) N-Terminal

<400> SEQUENCE: 5

```
Asn Asp Ala Glu Asp Cys Cys
1               5
```

<210> SEQ ID NO 6
<211> LENGTH: 6
<212> TYPE: PRT
<213> ORGANISM: Artificial Sequence
<220> FEATURE:
<223> OTHER INFORMATION: CCL19 (4-83) N-Terminal

<400> SEQUENCE: 6

```
Asp Ala Glu Asp Cys Cys
1               5
```

<210> SEQ ID NO 7
<211> LENGTH: 5
<212> TYPE: PRT
<213> ORGANISM: Artificial Sequence
<220> FEATURE:
<223> OTHER INFORMATION: CCL19 (5-83) N-Terminal

<400> SEQUENCE: 7

```
Ala Glu Asp Cys Cys
1               5
```

<210> SEQ ID NO 8
<211> LENGTH: 4
<212> TYPE: PRT
<213> ORGANISM: Artificial Sequence
<220> FEATURE:

```
<223> OTHER INFORMATION: CCL19 (6-83) N-Terminal

<400> SEQUENCE: 8

Glu Asp Cys Cys
1
```